United States Patent
Naar et al.

(10) Patent No.: US 10,626,395 B2
(45) Date of Patent: Apr. 21, 2020

(54) THERAPEUTIC TARGETING OF A MICRORNA TO TREAT DUCHENNE MUSCULAR DYSTROPHY

(71) Applicants: The General Hospital Corporation, Boston, MA (US); Aalborg University, Aalborg (DK)

(72) Inventors: Anders M. Naar, Arlington, MA (US); Sakari Kauppinen, Holte (DK); Andreas Petri, Frederiksberg (DK)

(73) Assignees: The General Hospital Corporation, Boston, MA (US); Aalborg University, Aalborg (DK)

( * ) Notice: Subject to any disclaimer, the term of this patent is extended or adjusted under 35 U.S.C. 154(b) by 0 days.

(21) Appl. No.: 16/345,635

(22) PCT Filed: Sep. 18, 2017

(86) PCT No.: PCT/US2017/052047
§ 371 (c)(1),
(2) Date: Apr. 26, 2019

(87) PCT Pub. No.: WO2018/080658
PCT Pub. Date: May 3, 2018

(65) Prior Publication Data
US 2019/0270993 A1 Sep. 5, 2019

Related U.S. Application Data

(60) Provisional application No. 62/523,923, filed on Jun. 23, 2017, provisional application No. 62/413,469, filed on Oct. 27, 2016.

(51) Int. Cl.
| | | |
|---|---|---|
| *C12N 15/113* | (2010.01) | |
| *A61K 31/713* | (2006.01) | |
| *A61K 31/7088* | (2006.01) | |
| *A61P 21/00* | (2006.01) | |
| *A61K 31/7115* | (2006.01) | |
| *A61K 31/711* | (2006.01) | |

(52) U.S. Cl.
CPC ........ *C12N 15/113* (2013.01); *A61K 31/7088* (2013.01); *A61K 31/711* (2013.01); *A61K 31/7115* (2013.01); *A61P 21/00* (2018.01); *C12N 2310/111* (2013.01); *C12N 2310/113* (2013.01); *C12N 2310/141* (2013.01); *C12N 2310/17* (2013.01); *C12N 2310/315* (2013.01); *C12N 2310/3231* (2013.01); *C12N 2320/35* (2013.01)

(58) Field of Classification Search
None
See application file for complete search history.

(56) References Cited

U.S. PATENT DOCUMENTS

| | | |
|---|---|---|
| 9,045,749 B2 | 6/2015 | Naar et al. |
| 9,476,046 B2 | 10/2016 | Naar et al. |
| 2006/0105360 A1 | 5/2006 | Croce et al. |
| 2010/0004320 A1 | 1/2010 | Elmen et al. |
| 2010/0292297 A1 | 11/2010 | Wang et al. |
| 2014/0051746 A1 | 2/2014 | Naar et al. |

OTHER PUBLICATIONS

Aartsma-Rus et al., "The importance of genetic diagnosis for Duchenne muscular dystrophy," Journal of Medical Genetics, Mar. 1, 2016, 53(3):145-51.
Alexander et al., "MicroRNA-199a is induced in dystrophic muscle and affects WNT signaling, cell proliferation, and myogenic differentiation," Cell Death and Differentiation, Sep. 2013, 20(9):1194-1208.
Alexander et al., "Regulation of DMD pathology by an ankyrin-encoded miRNA," Skeletal Muscle, Dec. 2011, 1(1):27, 17 Pages.
Al-Rewashdy et al., "Utrophin A is essential in mediating the functional adaptations of mdx mouse muscle following chronic AMPK activation," Human Molecular Genetics, Oct. 16, 2014, 24(5):1243-55.
Ambros, "The functions of animal microRNAs," Nature, Sep. 15, 2004, 431(7006):350-5.
Araki et al., "Targeted disruption of exon 52 in the mouse dystrophin gene induced muscle degeneration similar to that observed in Duchenne muscular dystrophy," Biochemical and Biophysical Research Communications, Sep. 18, 1997, 238(2):492-7.
Arany, "PGC-1 coactivators and skeletal muscle adaptations in health and disease," Current opinion in genetics & development, Oct. 1, 2008,18(5):426-34.
Baron et al., "Immune response and mitochondrial metabolism are commonly deregulated in DMD and aging skeletal muscle," PloS one, Nov. 9, 2011, 6(11):e26952, 11 Pages.
Bartel, "MicroRNAs: genomics, biogenesis, mechanism, and function," cell, Jan. 23, 2004,116(2):281-97.
Bartel, "MicroRNAs: target recognition and regulatory functions," cell, Jan. 23, 2009, 136(2):215-33.
Bastin et al., "Resveratrol and myopathy," Nutrients, May 2016, 8(5):254, 13 Pages.
Beastrom et al., "Mdx5Cv mice manifest more severe muscle dysfunction and diaphragm force deficits than do mdx mice," The American Journal of Pathology, Nov. 1, 2011, 179(5):2464-74.
Bonaldo et al., "Cellular and molecular mechanisms of muscle atrophy," Disease models & mechanisms, Jan. 1, 2013, 6(1):25-39.
Brolin et al., "Antisense mediated exon skipping therapy for duchenne muscular dystrophy (DMD)," Artificial DNA: PNA & XNA, Jan. 1, 2011, 2(1):6-15.
Bulfield et al., "X chromosome-linked muscular dystrophy (mdx) in the mouse," Proceedings of the National Academy of Sciences, Feb. 1, 1984,81(4):1189-92.
Burke et al., "Molecular profiling of dilated cardiomyopathy that progresses to heart failure," JCI Insight, May 5, 2016, 1(6), 18 Pages.

(Continued)

*Primary Examiner* — Tracy Vivlemore
(74) *Attorney, Agent, or Firm* — Fish & Richardson P.C.

(57) ABSTRACT

Methods of treating Duchenne muscular dystrophy (DMD) and Becker muscular dystrophy (BMD), comprising administering an inhibitory nucleic acid that targets miR-128.

24 Claims, 12 Drawing Sheets

Specification includes a Sequence Listing.

(56) References Cited

OTHER PUBLICATIONS

Camerino et al., "Gene expression in mdx mouse muscle in relation to age and exercise: aberrant mechanical-metabolic coupling and implications for pre-clinical studies in Duchenne muscular dystrophy," Human Molecular Genetics, Jun. 10, 2014, 23(21):5720-32.
Capogrosso et al., "Assessment of resveratrol, apocynin and taurine on mechanical-metabolic uncoupling and oxidative stress in a mouse model of Duchenne muscular dystrophy: A comparison with the gold standard, α-methyl prednisolone," Pharmacological Research, Apr. 1, 2016, 106:101-13.
Carnwath et al., "Muscular dystrophy in the mdx mouse: histopathology of the soleus and extensor digitorum longus muscles," Journal of the Neurological Sciences, Aug. 1, 1987, 80(1):39-54.
Chalkiadaki et al., "Muscle-specific SIRT1 gain-of-function increases slow-twitch fibers and ameliorates pathophysiology in a mouse model of Duchenne muscular dystrophy," PLoS Genetics, Jul. 17, 2014, 10(7):e1004490, 13 Pages.
Chamberlain et al., "Dystrophin-deficient mdx mice display a reduced life span and are susceptible to spontaneous rhabdomyosarcoma," The FASEB Journal, Jul. 2007, 21(9):2195-204.
Chan et al., "Post-natal induction of PGC-1α protects against severe muscle dystrophy independently of utrophin," Skeletal Muscle, Dec. 2014 Dec.;4(1):2, 13 Pages.
Chang et al., "Telomere shortening and metabolic compromise underlie dystrophic cardiomyopathy," Proceedings of the National Academy of Sciences, Nov. 15, 2016, 113(46):13120-5.
Chapman et al., "Recovery of induced mutations for X chromosome-linked muscular dystrophy in mice," Proceedings of the National Academy of Sciences, Feb. 1, 1989, 86(4):1292-6.
Choi et al., "Oxidative stress-mediated skeletal muscle degeneration: molecules, mechanisms, and therapies," Oxidative Medicine and Cellular Longevity, 2016, 2016, 13 Pages.
Dangain et al., "Muscle development in mdx mutant mice," Muscle & Nerve: Official Journal of the American Association of Electrodiagnostic Medicine, Dec. 1984, 7(9):700-4.
Danko et al., "The frequency of revertants in mdx mouse genetic models for Duchenne muscular dystrophy," Pediatric Research, Jul. 1992, 32(1):128-31.
De Arcangelis et al., "Pathways implicated in tadalafil amelioration of Duchenne muscular dystrophy," Journal of Cellular Physiology, Jan. 2016, 231(1):224-32.
De Palma et al., "Skeletal muscle homeostasis in duchenne muscular dystrophy: modulating autophagy as a promising therapeutic strategy," Frontiers in Aging Neuroscience, Jul. 24, 2014, 6:188, 8 Pages.
Elliott, "Diagnosis and management of dilated cardiomyopathy," Heart, Jul. 1, 2000, 84(1):106-12.
Fiacco et al., "Autophagy regulates satellite cell ability to regenerate normal and dystrophic muscles," Cell Death and Differentiation, Nov. 2016, 23(11):1839-49.
Flanigan et al., "Nonsense mutation-associated Becker muscular dystrophy: interplay between exon definition and splicing regulatory elements within the DMD gene," Human Mutation, Mar. 2011, 32(3):299-308.
Fletcher et al., "Targeted exon skipping to address "leaky" mutations in the dystrophin gene," Molecular Therapy-Nucleic Acids, Jan. 1, 2012, 1:e48.
Fukada et al., "Genetic background affects properties of satellite cells and mdx phenotypes," The American journal of pathology, May 1, 2010, 176(5):2414-24.
Garbincius et al., "Dystrophin-glycoprotein complex regulates muscle nitric oxide production through mechanoregulation of AMPK signaling," Proceedings of the National Academy of Sciences, Nov. 3, 2015, 112(44):13663-8.
Garry, "Dystrophin-deficient cardiomyopathy," Journal of the American College of Cardiology, May 31, 2016, 67(21):2533-46.
Geary et al., "Pharmacokinetics, biodistribution and cell uptake of antisense oligonucleotides," Advanced Drug Delivery Reviews, Jun. 29, 2015, 87:46-51.
Godin et al., "Peroxisome proliferator-activated receptor γ coactivator 1-α gene transfer restores mitochondrial biomass and improves mitochondrial calcium handling in post-necrotic mdx mouse skeletal muscle,"The Journal of physiology, Nov. 2012, 590(21):5487-502.
Goedeke et al., "MicroRNA-148a regulates LDL receptor and ABCA1 expression to control circulating lipoprotein levels," Nature Medicine, Nov. 2015, 21(11):1280, 14 Pages.
Gordon et al., "Resveratrol decreases inflammation and increases utrophin gene expression in the mdx mouse model of Duchenne muscular dystrophy," Clinical Nutrition, Feb. 1, 2013, 32(1):104-11.
Grounds et al., "Towards developing standard operating procedures for pre-clinical testing in the mdx mouse model of Duchenne muscular dystrophy,"Neurobiology of Disease, Jul. 1, 2008, 31(1):1-9, 19 Pages.
Guevel et al., "Quantitative proteomic analysis of dystrophic dog muscle," Journal of Proteome Research, Mar. 29, 2011, 10(5):2465-78.
Guiraud et al., "The pathogenesis and therapy of muscular dystrophies," Annual Review of Genomics and Human Genetics, Aug. 24, 2015, 16:281-308.
Guyon et al., "Modeling human muscle disease in zebrafish," Biochimica et Biophysica Acta (BBA)-Molecular Basis of Disease, Feb. 1, 2007, 1772(2):205-15.
Hafner et al., "Improved muscle function in Duchenne muscular dystrophy through l-arginine and metformin: an investigator-initiated, open-label, single-center, proof-of-concept-study," PloS one, Jan. 22, 2016, 11(1):e0147634, 19 Pages.
Handschin et al., "PGC-1α regulates the neuromuscular junction program and ameliorates Duchenne muscular dystrophy," Genes & development, Apr. 1, 2007, 21(7):770-83.
Handschin et al., "Skeletal muscle fiber-type switching, exercise intolerance, and myopathy in PGC-1α muscle-specific knock-out animals," Journal of Biological Chemistry, Oct. 12, 2007, 282(41):30014-21.
Hertel et al., "The expansion of the metazoan microRNA repertoire," BMC Genomics, Dec. 2006, 7(1):25.
Hollinger et al., "Rescue of dystrophic skeletal muscle by PGC-1α involves restored expression of dystrophin-associated protein complex components and satellite cell signaling," American Journal of Physiology-Regulatory, Integrative and Comparative Physiology, Apr. 17, 2013, 305(1):R13-23.
Hori et al., "Resveratrol ameliorates muscular pathology in the dystrophic mdx mouse, a model for Duchenne muscular dystrophy," Journal of Pharmacology and Experimental Therapeutics, Sep. 1, 2011, 338(3):784-94.
Im et al., "Differential expression of dystrophin isoforms in strains of mdx mice with different mutations," Human Molecular Genetics, Aug. 1, 1996, 5(8):1149-53.
Ji et al., "Downregulation of miRNA-128 sensitises breast cancer cell to chemodrugs by targeting Bax," Cell Biology International, Jul. 2013, 37(7):653-8.
Kauppinen et al., "Locked nucleic acid: high-affinity targeting of complementary RNA for Rnomics," RNA Towards Medicine, Springer, Berlin, Heidelberg, 2006, 405-22.
Kawahara et al., "Drug screening in a zebrafish model of Duchenne muscular dystrophy," Proceedings of the National Academy of Sciences, Mar. 29, 2011, 108(13):5331-6.
Kawahara et al., "Dystrophic muscle improvement in zebrafish via increased heme oxygenase signaling," Human Molecular Genetics, Nov. 13, 2013, 23(7):1869-78.
Khan et al., "Silencing myostatin using cholesterol-conjugated siRNAs induces muscle growth," Molecular Therapy-Nucleic Acids, Jan. 1, 2016, 5:e342, 9 Pages.
Kim et al., "Analysis of fatty infiltration and inflammation of the pelvic and thigh muscles in boys with Duchenne muscular dystrophy (DMD): grading of disease involvement on MR imaging and correlation with clinical assessments," Pediatric Radiology, Oct. 1, 2013 43(10):1327-35.
Kobayashi et al., "Sarcolemma-localized nNOS is required to maintain activity after mild exercise," Nature, Nov. 2008, 456(7221):511.

(56) References Cited

OTHER PUBLICATIONS

Kotelnikova et al., "Novel approach to meta-analysis of microarray datasets reveals muscle remodeling-related drug targets and biomarkers in Duchenne muscular dystrophy," PLoS Computational Biology, Feb. 2, 2012, 8(2):e1002365.

Kuno et al., "Resveratrol improves cardiomyopathy in dystrophin-deficient mice through SIRT1 protein-mediated modulation of p300 protein," Journal of Biological Chemistry, Feb. 22, 2013, 288(8):5963-72.

Kuno et al., "SIRT1: a novel target for the treatment of muscular dystrophies," Oxidative Medicine and Cellular Longevity, 2016, 2016.

Kuno et al., "The effects of resveratrol and SIRT1 activation on dystrophic cardiomyopathy," Annals of the New York Academy of Sciences, Aug. 2015, 1348(1):46-54.

Kyrychenko et al., "Mitochondrial dysfunctions during progression of dystrophic cardiomyopathy," Cell Calcium, Aug. 1, 2015, 58(2):186-95.

Lewis et al., "Conserved seed pairing, often flanked by adenosines, indicates that thousands of human genes are microRNA targets," Cell, Jan. 14, 2005, 120(1):15-20.

Lindow et al., "Discovering the first microRNA-targeted drug," Journal of Cell Biology, Oct. 29, 2012, 199, 407-12.

Liu et al., "Coupling of mitochondrial function and skeletal muscle fiber type by a miR-499/Fnip1/AMPK circuit," EMBO Molecular Medicine, Oct. 1, 2016, 8(10):1212-28.

Ljubicic et al., "AMP-activated protein kinase at the nexus of therapeutic skeletal muscle plasticity in Duchenne muscular dystrophy," Trends in Molecular Medicine, Oct. 1, 2013, 19(10):614-24.

Ljubicic et al., "Chronic AMPK activation evokes the slow, oxidative myogenic program and triggers beneficial adaptations in mdx mouse skeletal muscle," Human Molecular Genetics, Jun. 9, 2011, 20(17):3478-93.

Luk et al., "Dilated cardiomyopathy: a review," Journal of Clinical Pathology, Mar. 1, 2009, 62(3):219-25.

Maciotta et al., "Hmgb3 is regulated by microRNA-206 during muscle regeneration," PLoS one, Aug. 17, 2012, 7(8):e43464, 15 Pages.

McClorey et al., "Splicing intervention for Duchenne muscular dystrophy," Current Opinion in Pharmacology, Oct. 1, 2005, 5(5):529-34.

Miura et al., "Pharmacological activation of PPARβ/δ stimulates utrophin A expression in skeletal muscle fibers and restores sarcolemmal integrity in mature mdx mice," Human Molecular Genetics, Sep. 10, 2009, 18(23):4640-9.

Motohashi et al., "Identification of a novel microRNA that regulates the proliferation and differentiation in muscle side population cells," Stem Cells and Development, Apr. 27, 2012, 21(16):3031-43.

Motohashi et al., "Regulation of IRS1/Akt insulin signaling by microRNA-128a during myogenesis," Journal of Cell Science, Jun. 15, 2013, 126(12):2678-91.

Moulin et al., "Muscle redox disturbances and oxidative stress as pathomechanisms and therapeutic targets in early-onset myopathies," Seminars in Cell & Developmental Biology, Academic Press, Apr. 1, 2007, 64:213-23.

Muntoni et al., "Muscular weakness in the mdx mouse," Journal of the Neurological Science, Dec. 1, 1993, 120(1):71-7.

Najafi-Shoushtari et al., "MicroRNA-33 and the SREBP host genes cooperate to control cholesterol homeostasis," Science, Jun. 18, 2010, 328(5985):1566-9.

Nguyen et al., "Dilated Cardiomyopathy: Practice Essentials, Background, Pathophysiology," Medscape, Jan. 20, 2017, 26 Pages.

Obad et al., "Silencing of microRNA families by seed-targeting tiny LNAs," Nature Genetics, Apr. 2011, 43(4):371, 22 Pages.

Pal et al., "Src-dependent impairment of autophagy by oxidative stress in a mouse model of Duchenne muscular dystrophy," Nature Communications, Jul. 16, 2014, 5:4425, 10 Pages.

Pauly et al., "AMPK activation stimulates autophagy and ameliorates muscular dystrophy in the mdx mouse diaphragm," The American Journal of Pathology, Aug. 1, 2012, 181(2):583-92.

PCT International Preliminary Report on Patentability in International Appln. No. PCT/US2017/052047, dated Apr. 30, 2019, 10 pages.

PCT International Search Report for and Written Opinion in International Appln. PCT/US2017/052047, dated Jan. 23, 2018, 18 Pages.

Péladeau et al., "Combinatorial therapeutic activation with heparin and AICAR stimulates additive effects on utrophin A expression in dystrophic muscles," Human Molecular Genetics, Oct. 22, 2015, 25(1):24-43.

Percival et al., "Defects in mitochondrial localization and ATP synthesis in the mdx mouse model of Duchenne muscular dystrophy are not alleviated by PDE5 inhibition," Human Molecular Genetics, Oct. 9, 2012, 22(1):153-67.

Richardson, "Report of the 1995 World Health Organization/International Society and Federation of Cardiology Task Force on the definition and classification of cardiomyopathies," Circulation, 1996, 93:841, 9 Pages.

Rosenberg et al., "Immune-mediated pathology in Duchenne muscular dystrophy," Science Translational Medicine, Aug. 5, 2015, 7(299):299rv4, 13 Pages.

Rottiers et al., "MicroRNAs in metabolism and metabolic disorders," Nature Reviews Molecular Cell Biology, Apr. 2012, 13(4):239-50.

Rottiers et al., "Pharmacological inhibition of a microRNA family in nonhuman primates by a seed-targeting 8-mer antimiR," Science Translational Medicine, Nov. 20, 2013, 5(212):212ra162, 10 Pages.

Rybalka et al., "Defects in mitochondrial ATP synthesis in dystrophin-deficient mdx skeletal muscles may be caused by complex I insufficiency," PLoS one, Dec. 26, 2014, 9(12):e115763, 16 Pages.

Ryu et al., "NAD+ repletion improves muscle function in muscular dystrophy and counters global PARylation," Science Translational Medicine, Oct. 19, 2016, 8(361):361ra139, 15 Pages.

Sandri et al., "Misregulation of autophagy and protein degradation systems in myopathies and muscular dystrophies," Journal of Cell Science, Dec. 1, 2013, 126(23):5325-33.

Schuh et al., "Measuring mitochondrial respiration in intact single muscle fibers," American Journal of Physiology-Regulatory, Integrative and Comparative Physiology, Dec. 7, 2011, 302(6):R712-9, 10 Pages.

Scotti et al., "RNA mis-splicing in disease," Nature Reviews Genetics, Jan. 2016, 17(1):19-32.

Selsby et al., "Rescue of Dystrophic Skeletal Muscle by PGC-1α involves a fast to slow fiber type shift in the mdx mouse," PLoS one, Jan. 11, 2012, 7(1):e30063, 10 Pages.

Seno et al., "Transcriptomic analysis of dystrophin RNAi knockdown reveals a central role for dystrophin in muscle differentiation and contractile apparatus organization," BMC Genomics, Dec. 2010, 11(1):345, 12 Pages.

Serrano et al., "Fibrosis development in early-onset muscular dystrophies: mechanisms and translational implications," Seminars in Cell & Developmental Biology, Academic Press, Apr. 1, 2017, 64:181-90.

Siva et al., "Exon-skipping antisense oligonucleotides to correct missplicing in neurogenetic diseases," Nucleic Acid Therapeutics, Feb. 1, 2014, 24(1):69-86.

Spurney et al., "Preclinical drug trials in the mdx mouse: assessment of reliable and sensitive outcome measures," Muscle & Nerve: Official Journal of the American Association of Electrodiagnostic Medicine, May 2009, 39(5):591-602.

Stedman et al., "The mdx mouse diaphragm reproduces the degenerative changes of Duchenne muscular dystrophy," Nature, Aug. 1991, 352(6335):536-9.

Stenvang et al., "Inhibition of MicroRNA Function by AntimiR Oligonucleotides," Silence, Dec. 2012, 3(1):1, 17 Pages.

Syed et al., "Eteplirsen: first global approval," Drugs, Nov. 1, 2016, 76(17):1699-704.

Tan et al., "MicroRNA-128 governs neuronal excitability and motor behavior in mice," Science, Dec. 6, 2013, 342(6163):1254-8.

(56) References Cited

OTHER PUBLICATIONS

Tanabe et al., "Skeletal muscle pathology in X chromosome-linked muscular dystrophy (mdx) mouse," Acta Neuropathologica, Mar. 1, 1986, 69(1-2):91-5.

Terrill et al., "Oxidative stress and pathology in muscular dystrophies: focus on protein thiol oxidation and dysferlinopathies," The FEBS Journal, Sep. 2013, 280(17):4149-64.

Timpani et al., "Revisiting the dystrophin-ATP connection: How half a century of research still implicates mitochondrial dysfunction in Duchenne Muscular Dystrophy aetiology," Medical Hypotheses, Dec. 1, 2015, 85(6):1021-33.

Torres et al., "The mutant mdx: inherited myopathy in the mouse: morphological studies of nerves, muscles and end-plates," Brain, Apr. 1, 1987, 110(2):269-99.

Touznik et al., "New developments in exon skipping and splice modulation therapies for neuromuscular diseases," Expert Opinion on Biological Therapy, Jun. 1, 2014, 14(6):809-19.

Vallejo-Illarramendi et al., "Dysregulation of calcium homeostasis in muscular dystrophies," Expert Reviews in Molecular Medicine, 2014;16, 23 pages.

Van Rooij et al., "Development of microRNA therapeutics is coming of age," EMBO Molecular Medicine, Jul. 1, 2014, 6(7):851-64.

Van Westering et al., "Current understanding of molecular pathology and treatment of cardiomyopathy in Duchenne muscular dystrophy," Molecules, May 2015, 20(5):8823-55.

Vieira et al., "Jagged 1 rescues the Duchenne muscular dystrophy phenotype," Cell, Nov. 19, 2015, 163(5):1204-13.

Von Maltzahn et al., "Wnt7a treatment ameliorates muscular dystrophy," Proceedings of the National Academy of Sciences, Dec. 11, 2012, 109(50):20614-9.

Wagschal et al., "Genome-wide identification of microRNAs regulating cholesterol and triglyceride homeostasis," Nature Medicine, Nov. 2015, 21(11):1290, 25 Pages.

Whitehead et al., "Muscle damage in mdx (dystrophic) mice: role of calcium and reactive oxygen species," Clinical and Experimental Pharmacology and Physiology, Jul. 2006, 33(7):657-62.

Whitehead, "Enhanced autophagy as a potential mechanism for the improved physiological function by simvastatin in muscular dystrophy," Autophagy, Apr. 2, 2016, 12(4):705-6.

Widrick et al., "Muscle dysfunction in a zebrafish model of Duchenne muscular dystrophy," Physiological Genomics, Oct. 7, 2016, 48(11):850-60.

Wood et al., "RNA-targeted splice-correction therapy for neuromuscular disease," Brain, Feb. 11, 2010, 133(4):957-72.

```
LOCUS       NR_029672                  82 bp    RNA     linear   PRI 19-DEC-
2010
DEFINITION  Homo sapiens microRNA 128-1 (MIR128-1), microRNA.
ACCESSION   NR_029672
VERSION     NR_029672.1  GI:262205268
FEATURES             Location/Qualifiers
     source          1..82
                     /organism="Homo sapiens"
                     /mol_type="transcribed RNA"
                     /db_xref="taxon:9606"
                     /chromosome="2"
                     /map="2q21.3"
     gene            1..82
                     /gene="MIR128-1"
                     /gene_synonym="MIR128A; MIRN128-1; MIRN128A"
                     /note="microRNA 128-1"
                     /db_xref="GeneID:406915"
                     /db_xref="HGNC:31510"
                     /db_xref="MIM:611774"
                     /db_xref="miRBase:MI0000447"
     exon            1..82
                     /gene="MIR128-1"
                     /gene_synonym="MIR128A; MIRN128-1; MIRN128A"
                     /inference="alignment:Splign"
                     /number=1
     ncRNA           50..70
                     /gene="MIR128-1"
                     /gene_synonym="MIR128A; MIRN128-1; MIRN128A"
                     /ncRNA_class="miRNA"
                     /product="hsa-miR-128"
                     /db_xref="miRBase:MIMAT0000424"
                     /db_xref="GeneID:406915"
                     /db_xref="HGNC:31510"
                     /db_xref="MIM:611774"
                     /db_xref="miRBase:MI0000447"
ORIGIN
        1 tgagctgttg gattcggggc cgtagcactg tctgagaggt ttacatttct cacagtgaac
       61 cggtctcttt ttcagctgct tc  (SEQ ID NO:1)
```

```
tcacagtgaaccggtctcttt   (SEQ ID NO:2)

ucacagugaaccggucucuuu   (SEQ ID NO:3)
```

FIG. 3

```
       u   u        uuc        uag       cu           u
   gagc guugga   ggggccg    cacugu   gagaggu u
   |||| ||||||   |||||||    ||||||   ||||||
   uucg cgacuu   cucuggc    gugaca   cucuuua a
   c    u        uuu        caa      --       c
```

(SEQ ID NO:4)

FIG. 4

```
LOCUS       NR_029824                 84 bp    RNA     linear   PRI 20-SEP-
2010
DEFINITION  Homo sapiens microRNA 128-2 (MIR128-2), microRNA.
ACCESSION   NR_029824
VERSION     NR_029824.1  GI:262206021
FEATURES             Location/Qualifiers
     source          1..84
                     /organism="Homo sapiens"
                     /mol_type="transcribed RNA"
                     /db_xref="taxon:9606"
                     /chromosome="3"
                     /map="3p22.3"
     gene            1..84
                     /gene="MIR128-2"
                     /gene_synonym="mir-128b; MIR128B; MIRN128-2; MIRN128B"
                     /note="microRNA 128-2"
                     /db_xref="GeneID:406916"
                     /db_xref="HGNC:31511"
                     /db_xref="MIM:611769"
                     /db_xref="miRBase:MI0000727"
     exon            1..84
                     /gene="MIR128-2"
                     /gene_synonym="mir-128b; MIR128B; MIRN128-2; MIRN128B"
                     /inference="alignment:Splign"
                     /number=1
     ncRNA           52..72
                     /gene="MIR128-2"
                     /gene_synonym="mir-128b; MIR128B; MIRN128-2; MIRN128B"
                     /ncRNA_class="miRNA"
                     /product="hsa-miR-128"
                     /db_xref="miRBase:MIMAT0000424"
                     /db_xref="GeneID:406916"
                     /db_xref="HGNC:31511"
                     /db_xref="MIM:611769"
                     /db_xref="miRBase:MI0000727"
ORIGIN
        1 tgtgcagtgg gaaggggggc cgatacactg tacgagagtg agtagcaggt ctcacagtga
       61 accggtctct ttccctactg tgtc     (SEQ ID NO:5)
```

```
u ug        a           aua       ac      g gag
 g caguggg  aggggggccg   cacugu  gaga  u   u
 | |||||||  ||||||||||   ||||||  ||||  |
 u gucaucc  uuucucuggc   gugaca  cucu  g   a
c gu        c            caa     --     g acg
```

(SEQ ID NO:6)

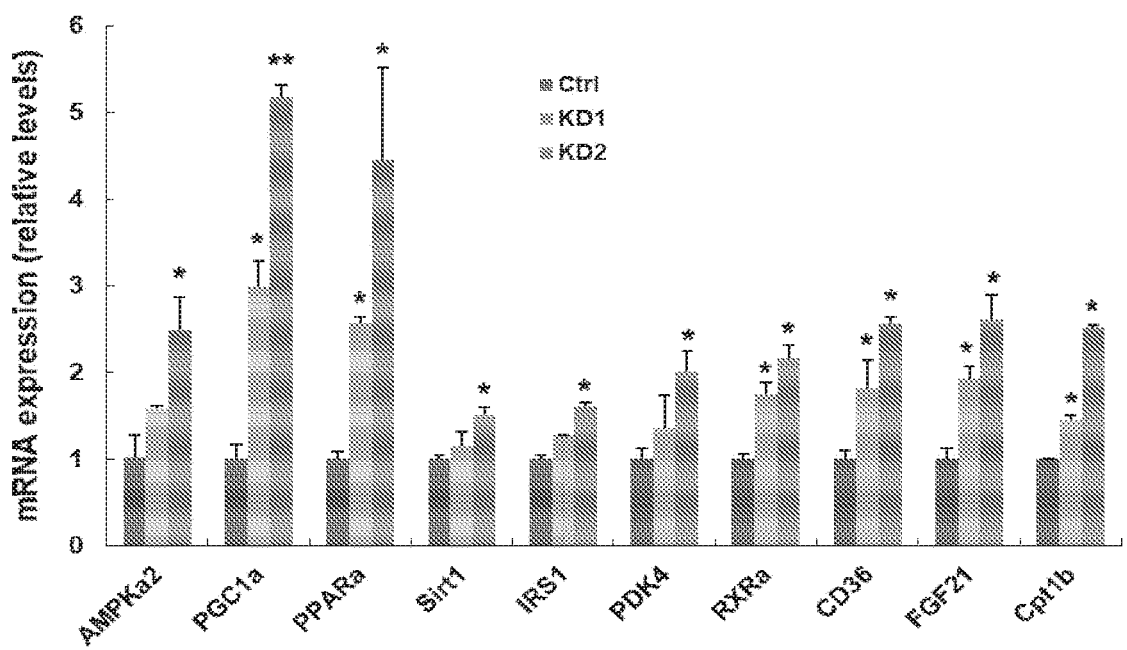
FIG. 7C
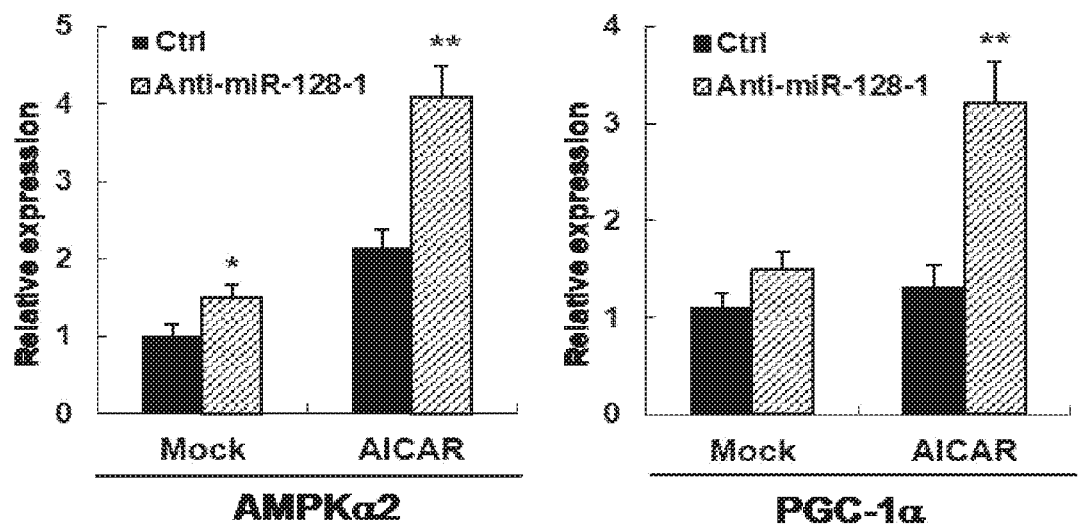
FIG. 8A
FIG. 8B

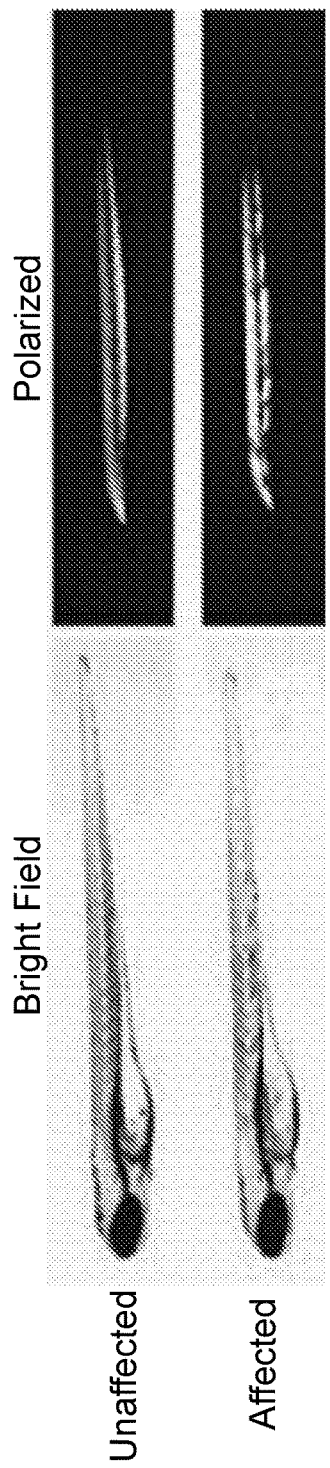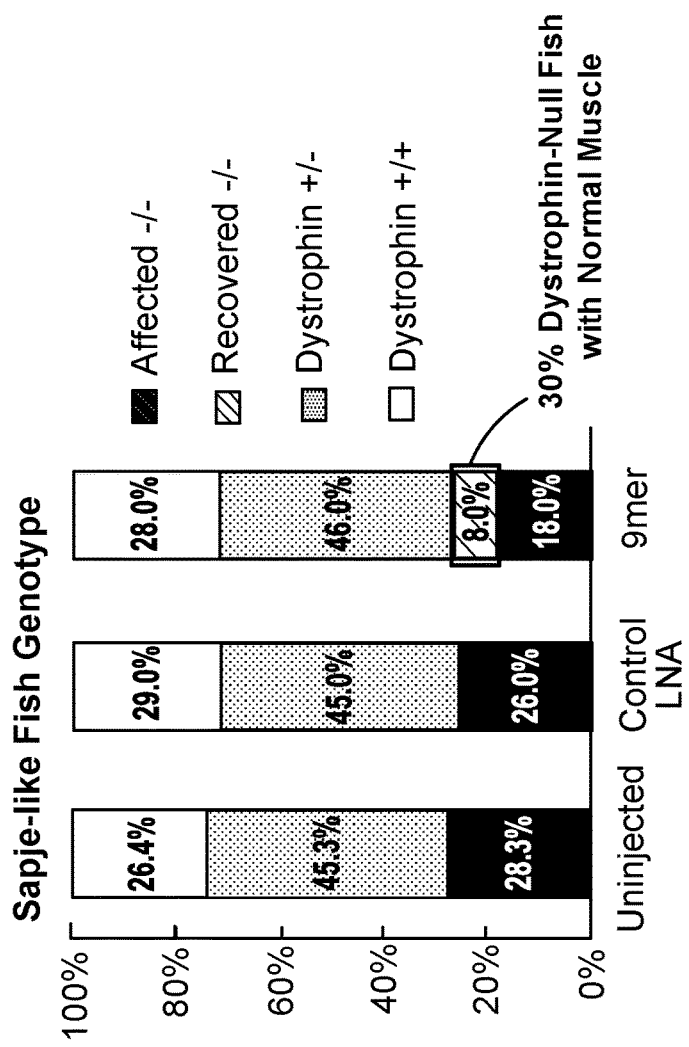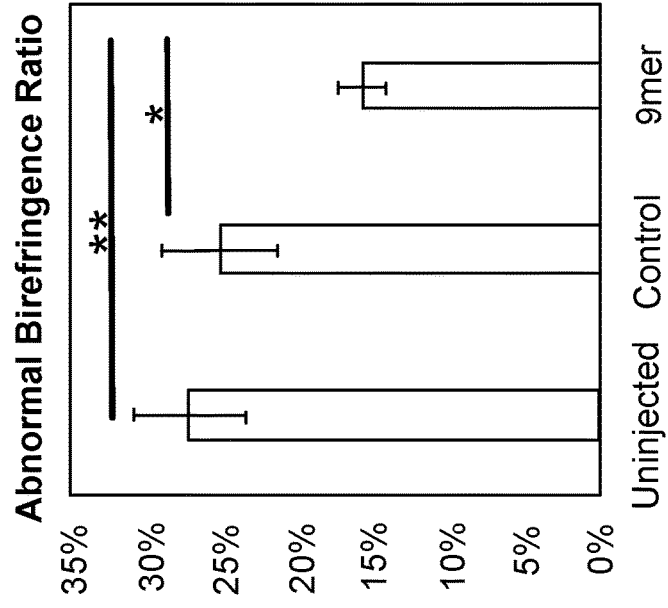
FIG. 9A
FIG. 9B
FIG. 9C

SEQUENCE LISTING

```
<160> NUMBER OF SEQ ID NOS: 11

<210> SEQ ID NO 1
<211> LENGTH: 82
<212> TYPE: DNA
<213> ORGANISM: Homo sapiens

<400> SEQUENCE: 1
tgagctgttg gattcggggc cgtagcactg tctgagaggt ttacatttct cacagtgaac     60
cggtctcttt ttcagctgct tc                                              82

<210> SEQ ID NO 2
<211> LENGTH: 21
<212> TYPE: DNA
<213> ORGANISM: Homo sapiens

<400> SEQUENCE: 2
tcacagtgaa ccggtctctt t                                               21

<210> SEQ ID NO 3
<211> LENGTH: 21
<212> TYPE: RNA
<213> ORGANISM: Homo sapiens

<400> SEQUENCE: 3
```
ucacagugaa ccggucucuu u					21

<210> SEQ ID NO 4
<211> LENGTH: 82
<212> TYPE: RNA
<213> ORGANISM: Homo sapiens

<400> SEQUENCE: 4
ugagcuguug gauucggggc cguagcacug ucugagaggu uuacauuucu cacagugaac			60 cggucucuuu uucagcugcu uc						82

<210> SEQ ID NO 5
<211> LENGTH: 84
<212> TYPE: DNA
<213> ORGANISM: Homo sapiens

<400> SEQUENCE: 5
tgtgcagtgg aaggggggc cgatacactg tacgagagtg agtagcaggt ctcacagtga			60 accggtctct ttccctactg tgtc						84

<210> SEQ ID NO 6
<211> LENGTH: 84
<212> TYPE: RNA
<213> ORGANISM: Homo sapiens

<400> SEQUENCE: 6
ugugcagugg aaggggggc cgauacacug uacgagagug aguagcaggu cucacaguga			60 accggugugu uugggacug ugcu						84

<210> SEQ ID NO 7
<211> LENGTH: 21
<212> TYPE: DNA
<213> ORGANISM: Homo sapiens

<400> SEQUENCE: 7
aaagagaccg gttcactgtg a							21

<210> SEQ ID NO 8
<211> LENGTH: 29
<212> TYPE: DNA
<213> ORGANISM: Artificial Sequence
<220> FEATURE:
<223> OTHER INFORMATION: 11-mer LNA targeting miR-128
<220> FEATURE:
<221> NAME/KEY: misc_feature
<222> LOCATION: (1)..(1)
<223> OTHER INFORMATION: LNA modification
<220> FEATURE:
<221> NAME/KEY: misc_feature
<222> LOCATION: (3)..(3)
<223> OTHER INFORMATION: PS link
<220> FEATURE:
<221> NAME/KEY: misc_feature
<222> LOCATION: (4)..(4)
<223> OTHER INFORMATION: LNA modification
<220> FEATURE:
<221> NAME/KEY: misc_feature
<222> LOCATION: (6)..(6)
<223> OTHER INFORMATION: PS link
<220> FEATURE:
<221> NAME/KEY: misc_feature
<222> LOCATION: (7)..(7)
<223> OTHER INFORMATION: LNA modification
<220> FEATURE:
<221> NAME/KEY: misc_feature
<222> LOCATION: (9)..(9)

```
<223> OTHER INFORMATION: PS link
<220> FEATURE:
<221> NAME/KEY: misc_feature
<222> LOCATION: (10)..(10)
<223> OTHER INFORMATION: LNA modification
<220> FEATURE:
<221> NAME/KEY: misc_feature
<222> LOCATION: (12)..(12)
<223> OTHER INFORMATION: PS link
<220> FEATURE:
<221> NAME/KEY: misc_feature
<222> LOCATION: (14)..(14)
<223> OTHER INFORMATION: PS link
<220> FEATURE:
<221> NAME/KEY: misc_feature
<222> LOCATION: (16)..(16)
<223> OTHER INFORMATION: PS link
<220> FEATURE:
<221> NAME/KEY: misc_feature
<222> LOCATION: (18)..(18)
<223> OTHER INFORMATION: PS link
<220> FEATURE:
<221> NAME/KEY: misc_feature
<222> LOCATION: (19)..(19)
<223> OTHER INFORMATION: LNA modification
<220> FEATURE:
<221> NAME/KEY: misc_feature
<222> LOCATION: (21)..(21)
<223> OTHER INFORMATION: PS link
<220> FEATURE:
<221> NAME/KEY: misc_feature
<222> LOCATION: (22)..(22)
<223> OTHER INFORMATION: LNA modification
<220> FEATURE:
<221> NAME/KEY: misc_feature
<222> LOCATION: (24)..(24)
<223> OTHER INFORMATION: PS link
<220> FEATURE:
<221> NAME/KEY: misc_feature
<222> LOCATION: (25)..(25)
<223> OTHER INFORMATION: LNA modification
<220> FEATURE:
<221> NAME/KEY: misc_feature
<222> LOCATION: (27)..(27)
<223> OTHER INFORMATION: PS link
<220> FEATURE:
<221> NAME/KEY: misc_feature
<222> LOCATION: (28)..(28)
<223> OTHER INFORMATION: LNA modification

<400> SEQUENCE: 8
ngnngnntnn tncnancnnt nngnntnng                                      29

<210> SEQ ID NO 9
<211> LENGTH: 9
<212> TYPE: RNA
<213> ORGANISM: Artificial Sequence
<220> FEATURE:
<223> OTHER INFORMATION: targeting sequence within human miR-128

<400> SEQUENCE: 9 cacagugaa                                                             9

<210> SEQ ID NO 10
<211> LENGTH: 9
<212> TYPE: DNA
<213> ORGANISM: Artificial Sequence
<220> FEATURE:
<223> OTHER INFORMATION: primary sequence of 9-mer Oligo targeting human
      miR-128

<400> SEQUENCE: 10 ttcactgtg                                                             9
```

```
<210> SEQ ID NO 11
<211> LENGTH: 11
<212> TYPE: DNA
<213> ORGANISM: Artificial Sequence
<220> FEATURE:
<223> OTHER INFORMATION: primary sequence of 11-mer Oligo targeting
      human miR-128,

<400> SEQUENCE: 11
ggttcactgt g                                                            11
```

THERAPEUTIC TARGETING OF A MICRORNA TO TREAT DUCHENNE MUSCULAR DYSTROPHY

CLAIM OF PRIORITY

This application is a § 371 National Stage Application of PCT/US2017/052047, filed Sept. 18, 2017, which claims the benefit of U.S. Provisional Application Ser. No. 62/413,469, filed on Oct. 27, 2016; and 62/523,923, filed on Jun. 23, 2017. The entire contents of the foregoing are incorporated herein by reference.

SEQUENCE LISTING

The instant application contains a Sequence Listing which has been submitted electronically in ASCII format and is hereby incorporated by reference in its entirety. Said ASCII copy, created on Sep. 18, 2017, is named 29539_0298WO1_SL.txt, and is 3,797 bytes in size.

TECHNICAL FIELD

Described herein are methods of treating Duchenne muscular dystrophy (DMD) and Becker muscular dystrophy (BMD), comprising administering an inhibitory nucleic acid that targets miR-128.

BACKGROUND

Duchenne muscular dystrophy (DMD), an X-linked inherited neuromuscular disorder, has a worldwide incidence of one in ~3,500 live male births, making it the most common muscular dystrophy. It is caused by mutations in the dystrophin gene, resulting in the progressive loss of skeletal and cardiac muscle. It is an early lethal disease, and most afflicted males die in their 20's or 30's due to cardiac or respiratory complications. In addition to steroids, which are able to modestly slow disease progression, an exon-skipping therapy was recently approved for the treatment of DMD. However, it only partly improves the symptoms of 13% of patients. There is thus an urgent need for novel therapeutic avenues for the treatment of DMD.

SUMMARY

The present invention is based, at least in part, on the discovery that miR-128-1 is a key regulator of mitochondrial metabolism in skeletal muscle cells and tissues through modulation of the expression of a number of proteins implicated in DMD, such as PGC-1α, SIRT1, AMPKα2, CPT1β and PPARα. miR-128-1 is also predicted to target JAG1, as well as the autophagy factor ULK1, and WNT7A, whose over-expression also improves DMD phenotypes in mdx mice. Potent positive effects were observed after miR-128-1 locked nucleic acid (LNA) antisense oligonucleotide (ASO) treatment on the energy expenditure program in murine C2C12 myotubes, and increased numbers of mitochondria and elevated energy expenditure gene expression (e.g., PGC-1α, SIRT1, AMPKα2, PPARα, and UCP3) were seen in skeletal muscle in mice. In addition, as shown herein, LNA ASOs targeting miR-128-1 in zebrafish (fish miR-128-1 is identical to mouse and human) strongly ameliorated skeletal muscle-related phenotypes in the sapje-like dystrophin-deficient zebrafish model, resulting in a marked decrease in skeletal muscle abnormalities and rescue of swim velocity/distance to near wild-type levels. Finally, injection of anti-miR-128-1 LNA ASOs in mdx mice decreased pathological muscle phenotypes in this model. Thus miR-128-1 is a target for highly potent and specific LNA ASO therapeutics for the treatment of DMD.

This provided herein are methods for treating a subject who has Duchenne muscular dystrophy (DMD) or Becker muscular dystrophy (BMD). The methods include administering to the subject a therapeutically effective amount of an inhibitory nucleic acid that is complementary to all or part of any of SEQ ID NOs: 1-6.

Also provided herein are methods for increasing muscle mass, or reducing or delaying muscle loss, e.g., in a subject who has Duchenne muscular dystrophy (DMD) or Becker muscular dystrophy (BMD). The methods include administering to the subject a therapeutically effective amount of an inhibitory nucleic acid that is complementary to all or part of any of SEQ ID NOs:1-6.

Further, provided herein are methods for treating, or reducing risk of developing, dilated cardiomyopathy (DCM) in a subject, e.g., wherein the subject has Duchenne muscular dystrophy (DMD) or Becker muscular dystrophy (BMD). The methods include administering to the subject an inhibitory nucleic acid sequence that is complementary to all or part of any of SEQ ID NOs:1-6.

In some embodiments, the inhibitory nucleic acid is complementary to all or part of SEQ ID NO:2.

In some embodiments, the inhibitory nucleic acid is complementary to at least nucleotides 2-7 (5'-CACAGU-3') of SEQ ID NO:3.

In some embodiments, the inhibitory nucleic acid is an antisense oligonucleotide.

In some embodiments, the antisense oligonucleotide comprises a sequence that is complementary to SEQ ID NO:3.

In some embodiments, the inhibitory nucleic acid is an interfering RNA.

In some embodiments, the interfering RNA is a small hairpin RNA (shRNA) or small interfering RNA (siRNA).

In some embodiments, the inhibitory nucleic acid sequence inhibits post-transcriptional processing of SEQ ID NO:1 or 5.

In some embodiments, the subject has DMD or BMD.

In some embodiments, the methods include selecting a subject on the basis that they have DMD or BMD.

In some embodiments, the inhibitory nucleic acid has at least one locked nucleotide.

In some embodiments, the inhibitory nucleic acid has a phosphorothioate backbone.

In some embodiments, the inhibitory nucleic acid is or comprises

```
                              (SEQ ID NO: 10)
         TTCACTGTG
         or
                              (SEQ ID NO: 11)
         GGTTCACTGTG,
```

In some embodiments, at least half of the nucleic acids are locked

In some embodiments, all of the nucleic acids are locked.

In some embodiments, the backbone is a phosphorothioate backbone.

In some embodiments, the inhibitory nucleic acid is or comprises (SEQ ID NO: 8)
+G*+G*+T*+T*C*A*C*+T*+G*+T*+G.

In some embodiments, the inhibitory nucleic acid is administered at a dose of 1-20 mg/kg.

In some embodiments, the inhibitory nucleic acid is administered once or twice per month.

Also provided herein are inhibitory nucleic acids that are or comprise +G*+G*+T*+T*C*A*C*+T*+G*+T*+G (SEQ ID NO:8), as well as pharmaceutical compositions comprising the inhibitory nucleic acids described herein.

In addition, provided herein are inhibitory nucleic acids that are complementary to all or part of any of SEQ ID NOs: 1-6 for use in a method of treating a subject who has Duchenne muscular dystrophy (DMD) or Becker muscular dystrophy (BMD); for use in a method of increasing muscle mass, or reducing or delaying muscle loss, in a subject who has Duchenne muscular dystrophy (DMD) or Becker muscular dystrophy (BMD); or for use in a method of treating, or reducing risk of developing, dilated cardiomyopathy (DCM) in a subject who has Duchenne muscular dystrophy (DMD) or Becker muscular dystrophy (BMD). In some embodiments, the inhibitory nucleic acid is or comprises (SEQ ID NO: 8)
+G*+G*+T*+T*C*A*C*+T*+G*+T*+G.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1 shows the sequence of human miR-128-1 precursor, also known as miR-128A precursor (SEQ ID NO:1).

FIG. 2 shows the sequence of mature human miR-128 DNA (SEQ ID NO:2) and RNA (SEQ ID NO:3). The mature sequences are the same for miR-128-1 and miR-128-2.

FIG. 3 shows the predicted hairpin structure of miR-128-1 precursor RNA (SEQ ID NO:4).

FIG. 4 shows the sequence of human miR-128-2 precursor, also known as miR-128B precursor (SEQ ID NO:5).

FIGS. 7A-C. Anti-miR-128-1 treatment of C2C12 myotubes results in knock-down of miR-128-1 (7A) and elevated expression of genes involved in mitochondrial biogenesis and energy expenditure (7B, 7C), a number of which have been implicated as modifiers downstream of dystrophin loss in DMD.

FIGS. 8A-F. Anti-miR-128-1 treatment of C2C12 cells results in increased potency of the AMPK activator AICAR and in increased mitochondrial energy expenditure. 8A-D. Increased AICAR-stimulated expression of AMPKα2, PGC-la, PPARα, and CPT1β in response to anti-miR-128-1 treatment of C2C12 myoblasts. 8E. Elevated mitochondrial respiration in C2C12 cells after anti-miR-128-1 treatment, as determined by Seahorse analysis. 8F. Increased fatty acid β-oxidation in C2C12 cells in response to anti-miR-128-1 treatment.

FIGS. 9A-C 9mer-LNA inhibiting miR128 restored sapje-like fish muscle phenotype. 9A. Representative picture of affected fish birefringence. 9B. 9mer consistently reduced the ratio of affected fish in progeny. 9C. Sequencing confirmed the restoring of muscle structure after 9mer LNA treatment.

DETAILED DESCRIPTION

Figures 5, 6A:
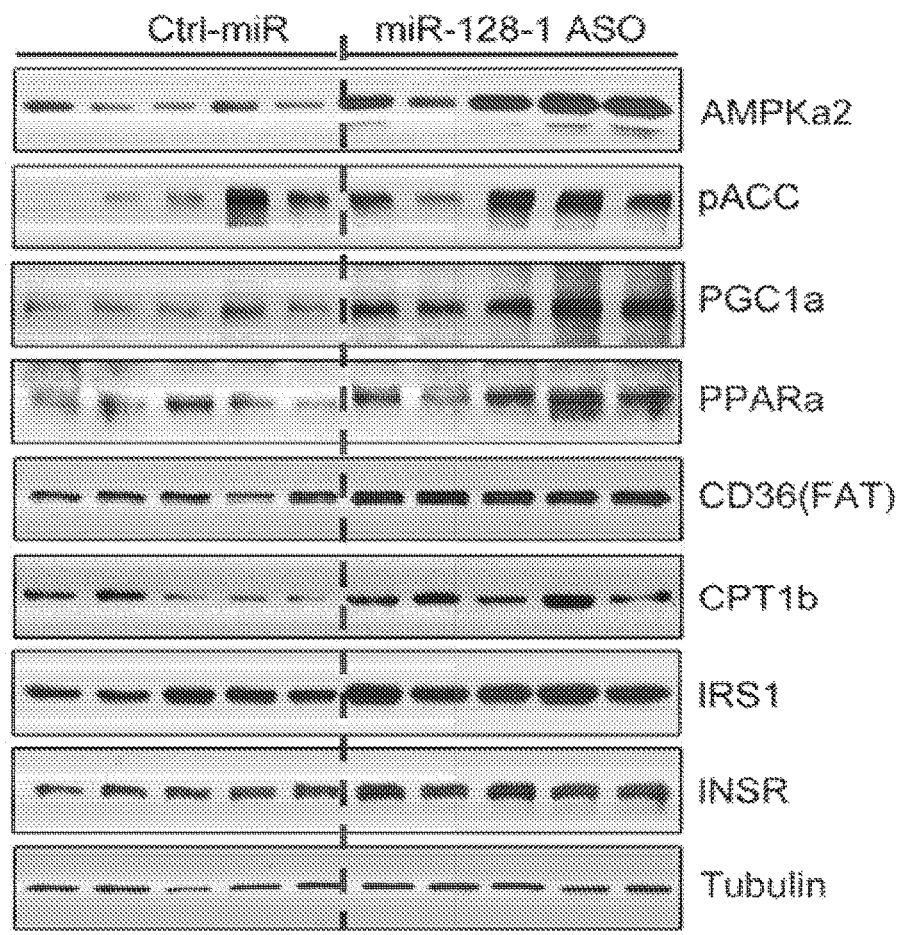
FIG. 5 shows the predicted hairpin structure of miR-128-2 precursor RNA (SEQ ID NO:6).
FIGS. 6A-C. AntimiR-128-1 treatment of diet-induced obese (DIO) mice results in elevated expression of genes involved in mitochondrial biogenesis and energy expenditure (6A, 6B), and increased numbers of mitochondria (6C) in skeletal muscle.

Duchenne muscular dystrophy (DMD) and Becker muscular dystrophy (BMD) are inherited progressive muscle disorders that are non-inflammatory and not associated with a central or peripheral nerve abnormality. The disease affects the muscles with definite fiber degeneration but without evidence of morphologic aberrations, resulting in progressive muscle wasting, and are caused by defects in the dystrophin gene DMD. See, e.g., Aartsma-Rus et al., J Med Genet. 2016 March; 53(3):145-51; Flanigan et al., Hum Mutat. 2011 March; 32(3): 299-308. In some cases, DMD or BMD are caused by mutations that affect splicing of the transcript, e.g., acceptor or donor splice site mutations.

Dilated cardiomyopathy (DCM) is a progressive disease of the cardiac muscle characterized by ventricular chamber enlargement and contractile dysfunction (See, e.g., Nguyen et al., *Dilated Cardiomyopathy*, 2017, available at emedicine.medscape.com/article/152696-overview; Richardson et al., Circulation. 1996; 93(5):841; Elliott, Heart. 2000; 84(1): 106; Luk et al., J Clin Pathol. 2009; 62(3):219. DCM is a late manifestation in DMD, with >90% of older boys showing symptoms, and a leading cause of heart failure and death (see, e.g., Kamdar and Garry, J. Amer. Coll. Cardiol. 2016 May 31(67): 2533-46). Recent findings have suggested that down-regulation of PPARalpha and PGC1alpha/beta in cardiac muscle in DCM leads to decreased mitochondrial function and oxidative stress that significantly contributes to the DCM pathologies (e.g., Burke et al. JCI Insight 2016; 1(6):e86898; Chang et al. PNAS 2016 Nov. 15(113): 13120-25).

A number of therapeutic strategies for DMD/BMD are currently being pursued, including approaches that attempt to ameliorate the splicing errors or target the secondary deleterious effects downstream of dystrophin deficiency, such as abnormal mitochondrial metabolism and autophagy.

Glucocorticoid treatment remains the standard of care for DMD, but exhibits limited efficacy and long-term use is associated with moderate to serious side effects such as immune suppression, weight gain, bone loss and abnormal glucose regulation[1]. A number of new approaches to the treatment of DMD are being pursued[1], including strategies to restore dystrophin such as exon-skipping antisense oligonucleotide (ASO) therapies, CRSPR-Cas9-based corrective mutagenesis, and virus-based dystrophin replacement. Although much excitement greeted the recent FDA approval of an exon-skipping therapy for DMD produced by Sarepta Therapeutics, this treatment only modestly improves ambulation as it generates a truncated and partially functional dystrophin protein akin to that found in the milder Becker-type of muscular dystrophy[2]. Moreover, it is limited to the ~13% of patients that have mutations where skipping exon 51 will restore the dystrophin translational reading frame and produce protein. The lack of efficacious treatments for most DMD patients highlights an urgent need for novel therapeutic interventions for this devastating disease.

miRNAs are short (~18-24 nucleotide) non-coding RNAs with diverse functions in development, metabolism and disease[53]. They regulate gene expression by base-pairing with partially complementary sequences primarily located in the 3'UTRs of target mRNAs and thereby promote mRNA degradation or translational repression[54-57]. Each miRNA has the potential to target a large number of mRNAs as predicted by complementarity to the miRNA seed region and non-seed sequences[55], and frequently control multiple genes in linked pathways, thereby exerting a larger cumulative effect. Owing to their short but highly specific sequence recognition motifs and, not uncommonly, marked regulatory impact on pathways important in physiology and disease, miRNAs represent attractive targets of potent and highly sequence-selective antisense oligonucleotides (ASOs).

As shown herein, miR-128-1 directly targets PPARalpha and PGC1alpha in skeletal muscle, accompanied by down-regulation of mitochondrial biogenesis and function (see the Examples), with LNA ASO treatment ameliorating these defects in DMD. In addition, as the heart is also a striated muscle, it is believed that miR-128-1 plays a pathological role in DCM in general, but in particular in the context of DMD.

Methods of Treatment

The methods described herein include the inhibition of miR-128 in a subject who has DMD or BMD, and/or has DCM, to thereby treat the subject. For example, the methods can achieve a therapeutic effect, e.g., reduction in muscle weakness or a reduction in rate of muscle loss or weakening; increasing muscle mass; reducing or delaying muscle loss; or treating, or reducing risk of developing, DCM, e.g., in a subject who has DMD or BMD. This can be achieved, for example, by administering an inhibitory nucleic acid, e.g., an antisense oligonucleotide that is complementary to miR-128, including but not limited to an antisense oligonucleotide comprising all or part of AAAGAGACCGGTTCACTGTGA (SEQ ID NO:7); in some embodiments, as described in further detail below, the oligo includes different modifications, e.g., in the sugar backbone, to make it more cell permeable and nuclease resistant on one hand, and physiologically non-toxic at low concentrations on the other.

In some embodiments, the oligo is an LNA comprising the sequence (SEQ ID NO: 8)
+G*+G*+T*+T*C*A*C*+T*+G*+T*+G

* indicates PS link
+ indicates LNA modification

Other inhibitory nucleic acids for use in practicing the methods described herein and that are complementary to miR-128 can be those that inhibit post-transcriptional processing of miR-128, such as an interfering RNA, including but not limited to an shRNA or siRNA, or an antagomir.

Inhibitory Nucleic Acids

Inhibitory nucleic acids useful in the present methods and compositions include antisense oligonucleotides, modified bases/locked nucleic acids (LNAs), antagomirs, peptide nucleic acids (PNAs), and other oligomeric compounds or oligonucleotide mimetics which hybridize to at least a portion of the target nucleic acid (i.e., miR-128, e.g., all or part of any of SEQ ID NOs:1-6) and modulate its function; see, e.g., U.S. Pat. Nos. 9,045,749 and 9,476,046. In some embodiments, the inhibitory nucleic acids include antisense RNA, antisense DNA, chimeric antisense oligonucleotides, antisense oligonucleotides comprising modified linkages, or combinations thereof. See, e.g., WO 2010040112.

In some embodiments, the inhibitory nucleic acids are 9 to 50, 9 to 21, 13 to 50, or 13 to 30 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length. In some embodiments, the antisense or oligonucleotide compounds of the invention are 12 or 13 to 30 nucleotides in length. One having ordinary skill in the art will appreciate that this embodies inhibitory nucleic acids having antisense portions of 12, 13, 14, 15, 16, 17, 18, 19, 20, 21, 22, 23, 24, 25, 26, 27, 28, 29 or 30 nucleotides in length, or any range therewithin.

In some embodiments, the inhibitory nucleic acids are designed to target a specific region of miR-128. For example, a specific functional region can be targeted, e.g., a region comprising a seed sequence or a region complementary to the target nucleic acid on which the miR-128 acts. For example, the inhibitory nucleic acid can be designed to target at least nucleotides 2-10 of the mature miR-128-1, e.g., complementary to CACAGUGAA (SEQ ID NO:9), e.g., have the sequence TTCACTGTG (SEQ ID NO:10, which is the same as nucleotides 12-20 of SEQ ID NO:7). Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

In some embodiments, the inhibitory nucleic acids are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. In some embodiments, the oligonucleotide is a gapmer (contain a central stretch (gap) of DNA monomers sufficiently long to induce RNase H cleavage, flanked by blocks of LNA modified nucleotides; see, e.g., Stanton et al., Nucleic Acid Ther. 2012. 22: 344-359; Nowotny et al., Cell, 121:1005-1016, 2005; Kurreck, European Journal of Biochemistry 270:1628-1644, 2003; Fluiter et al., Mol Biosyst. 5(8):838-43, 2009). In some embodiments, the oligonucleotide is a mixmer (includes alternating short stretches of LNA and DNA; Naguibneva et al., Biomed Pharmacother. 2006 November; 60(9):633-8; Orom et al., Gene. 2006 May 10; 3720:137-41). Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, $CH_2$~N($CH_3$)~O~$CH_2$ (known as a methylene(methylimino) or MMI backbone], $CH_2$—O—N($CH_3$)—$CH_2$, $CH_2$—N($CH_3$)—N($CH_3$)—$CH_2$ and O—N($CH_3$)— $CH_2$—$CH_2$ backbones, wherein the native phosphodiester backbone is represented as O— P—O—$CH_2$,); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991.

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts; see U.S. Pat. Nos. 5,034,506; 5,166,315; 5,185,444; 5,214,134; 5,216,141; 5,235,033; 5,264, 562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, $SCH_3$, F, OCN, $OCH_3OCH_3$, $OCH_3O(CH_2)n$ $CH_3$, $O(CH_2)n$ $NH_2$ or $O(CH_2)n$ $CH_3$ where n is from 1 to about 10; Ci to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; $SOCH3$; $SO2$ $CH3$; $ONO2$; $NO2$; $N3$; $NH2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-0-$CH_2CH_2OCH_3$, also known as 2'-O-(2-methoxyethyl)] (Martin et al, Helv. Chim. Acta, 1995, 78, 486). Other preferred modifications include 2'-methoxy (2'-0-$CH_3$), 2'-propoxy (2'-$OCH_2CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-77; Gebeyehu, G, et al. Nucl. Acids Res. 1987, 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130, 302; 5,134,066; 5,175, 273; 5,367,066; 5,432,272; 5,457, 187; 5,459,255; 5,484,908; 5,502,177; 5,525,711; 5,552, 540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552, 538; 5,578,717, 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391, 723; 5,416,203, 5,451,463; 5,510,475; 5,512,667; 5,514,785; 5,565,552; 5,567,810; 5,574,142; 5,585,481; 5,587,371; 5,595,726; 5,597,696;

5,599,923; 5,599, 928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The inhibitory nucleic acids useful in the present methods are sufficiently complementary to all or part of miR-128, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a miR-128 sequence, then the bases are considered to be complementary to each other at that position. 100% complementarity is not required.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. The inhibitory nucleic acids and the miR-128 are complementary to each other when a sufficient number of corresponding positions in each molecule are occupied by nucleotides that can hydrogen bond with each other. Thus, "specifically hybridizable" and "complementary" are terms which are used to indicate a sufficient degree of complementarity or precise pairing such that stable and specific binding occurs between the inhibitory nucleic acid and the miR-128 target sequence. For example, if a base at one position of an inhibitory nucleic acid is capable of hydrogen bonding with a base at the corresponding position of a miR-128 molecule, then the bases are considered to be complementary to each other at that position.

Although in some embodiments, 100% complementarity is desirable, it is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target miR-128 molecule interferes with the normal function of the target miR-128 to cause a loss of activity, and there is a sufficient degree of complementarity to avoid non-specific binding of the sequence to non-target miR-128 sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., *Molecular Cloning: A Laboratory Manual*, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within miR-128 (e.g., a target region comprising the seed sequence). For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Antisense and other compounds of the invention that hybridize to a miR-128 target sequence are identified through routine experimentation. In general the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to a miR-128 target sequence. Thus, oligonucleotides are chosen that are sufficiently complementary to the target, i.e., that hybridize sufficiently well and with sufficient specificity, to give the desired effect.

Modified Bases/Locked Nucleic Acids (LNAs)

In some embodiments, the inhibitory nucleic acids used in the methods described herein comprise one or more modified bonds or bases. Modified bases include phosphorothioate, methylphosphonate, peptide nucleic acids, or locked nucleic acid (LNA) molecules. Preferably, the modified nucleotides are locked nucleic acid molecules, including [alpha]-L-LNAs. LNAs comprise ribonucleic acid analogues wherein the ribose ring is "locked" by a methylene bridge between the 2'-oxygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a miR-128 target sequence. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of the LNA (or any other inhibitory nucleic acid described herein); for example, a series of oligonucleotides of 10-30 nucleotides spanning the length of a target miR-128 sequence can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of three or more Gs or Cs, or more than four LNA residues, should be avoided where possible (for example, it may not be possible with very short (e.g., about 9-10 nt) oligonucleotides). In some embodiments, the LNAs are xylo-LNAs.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

In some embodiments of the methods described herein, the inhibitory nucleic acid is or comprises TTCACTGTG (SEQ ID NO:10) or GGTTCACTGTG (SEQ ID NO:11), wherein all or some of the nucleic acids are locked and the backbone is a phosphorothioate backbone (e.g., all locked in SEQ ID NO:9 and some (e.g., at least 50%) locked in SEQ ID NO:10). In some embodiments of the methods described herein, the inhibitory nucleic acid is or comprises SEQ ID NO:8.

Antagomirs

In some embodiments, the antisense is an antagomir. Antagomirs are chemically modified antisense oligonucleotides that target a miR-128 target sequence. For example, an antagomir for use in the methods described herein can include a nucleotide sequence sufficiently complementary to hybridize to a miR-128 target sequence of about 12 to 25 nucleotides, preferably about 15 to 23 nucleotides.

In general, antagomirs include a cholesterol moiety, e.g., at the 3'-end. In some embodiments, antagomirs have various modifications for RNase protection and pharmacologic properties such as enhanced tissue and cellular uptake. For example, In addition to the modifications discussed above for antisense oligos, an antagomir can have one or more of complete or partial 2'-O-methylation of sugar and/or a phosphorothioate backbone. Phosphorothioate modifications provide protection against RNase activity and their lipophilicity contributes to enhanced tissue uptake. In some embodiments, the antagomir can include six phosphorothioate backbone modifications; two phosphorothioates are located at the 5'-end and four at the 3'-end. See, e.g., Krutzfeldt et al., Nature 438, 685-689 (2005); Czech, N Engl J Med 2006; 354:1194-1195 (2006); Robertson et al., Silence. 1:10 (2010); Marquez and McCaffrey, Hum Gene Ther. 19(1):27-38 (2008); van Rooij et al., Circ Res. 103 (9):919-928 (2008); and Liu et al., Int. J. Mol. Sci. 9:978-999 (2008). Antagomirs useful in the present methods can also be modified with respect to their length or otherwise the number of nucleotides making up the antagomir. The antagomirs must retain specificity for their target, i.e., must not directly bind to, or directly significantly affect expression levels of, transcripts other than the intended target.

In some embodiments, the inhibitory nucleic acid is locked and includes a cholesterol moiety (e.g., a locked antagomir).

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., *Molecular Cloning; A Laboratory Manual* 3d ed. (2001); *Current Protocols in Molecular Biology*, Ausubel et al., eds. (John Wiley & Sons, Inc., New York 2010); Kriegler, *Gene Transfer and Expression: A Laboratory Manual* (1990); *Laboratory Techniques In Biochemistry And Molecular Biology: Hybridization With Nucleic Acid Probes, Part I Theory and Nucleic Acid Preparation*, Tijssen, ed. Elsevier, N.Y. (1993).

Pharmaceutical Compositions

The methods described herein can include the administration of pharmaceutical compositions and formulations comprising inhibitory nucleic acid sequences designed to target miR-128.

In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., *Remington: The Science and Practice of Pharmacy*, 21st ed., 2005.

The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for parenteral administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form can vary depending upon the host being treated, the particular mode of administration. The amount of active ingredient which can be combined with a carrier material to produce a single dosage form will generally be that amount of the compound which produces a therapeutic effect, e.g., reduction in miR-128 levels and/or reduction in a symptom of DMD, BMD, or DCM.

Pharmaceutical formulations of this invention can be prepared according to any method known to the art for the manufacture of pharmaceuticals. Such drugs can contain, for example, preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, controlled release formulations, on patches, in implants, etc. Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences as described herein. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

In some embodiments, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. 20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The formulations of the invention can be administered for prophylactic and/or therapeutic treatments. In some embodiments, for therapeutic applications, compositions are administered to a subject who is need of reduced triglyceride levels, or who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to decrease serum levels of triglycerides in the subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; Remington: The Science and Practice of Pharmacy, 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

The specificity, stability and safety of ASO technologies have improved dramatically over the last 5-10 years[67]. Various studies have reported successful mammalian dosing using complementary nucleic acid sequences. For example, Esau C., et al., (2006) Cell Metabolism, 3(2):87-98 reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾ 45, ALT ¾ 35) for all doses with the exception of the 75 mg/kg dose of miR-122 ASO, which showed a very mild increase in ALT and AST levels. They concluded that 50 mg/kg was an effective, non-toxic dose. Another study by Krutzfeldt J., et al., (2005) Nature 438, 685-689, injected antagomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen J., et al., (2008) Nature 452, 896-899, report that efficient silencing of miR-122 was achieved in primates by three doses of 10 mg kg-1 LNA-anti-miR, leading to a long-lasting and reversible decrease in total plasma cholesterol without any evidence for LNA-associated toxicities or histopathological changes in the study animals.

In preferred embodiments, Locked Nucleic Acid (LNA) ASO technology is used to target miR-128 in DMD. The LNA chemistry affords strongly increased target affinity and specificity, and is combined with a phosphorothioate backbone of the ASO for increased in vivo stability and pharmacokinetics[68]. This ASO chemistry also compares favorably with older technologies such as morpholino-based chemistries. Terminal LNA ASO half-life in circulation is typically 2-3 weeks in mammals, based on multiple studies in mice and non-human primates with an LNA ASO targeting miR-33 (e.g., Rottiers et al. Science Transl. Med. 2013[61]), with LNAASOs detected in tissues up to 7 weeks after a single injection. This allows once-weekly subcutaneous injection in mice, and possibly once-monthly subcutaneous dosing in humans due to decreased kidney clearance of LNAASOs in humans as compared with rodents. In miR-128-1 LNA ASO studies with once-weekly subcutaneous delivery at 2.5-10 mg/kg in several mouse models of cardiometabolic disease (obesity, Type 2 diabetes, NAFLD/NASH, atherosclerosis), strong target engagement was observed in all major metabolic tissues, including skeletal muscle, liver, subcutaneous and visceral WAT, and BAT, with profound beneficial effects on whole animal metabolism (Wagschal et al. Nature Med. 2015[62] and unpublished data). Additionally, no significant elevation of liver and kidney toxicity parameters was observed, suggesting that anti-miR-128-1 LNA ASO treatment is well tolerated, at least in mice. In some embodiments, the methods include the administration of 1-10 mg/kg, 2-5 mg/kg, about 1×/month, 2×/month, or 1×/week.

In some embodiments, the methods described herein can include co-administration with other drugs or pharmaceuticals, e.g., compositions for treating DMD. For example, the inhibitory nucleic acids can be co-administered with drugs for treating or reducing risk of a disorder described herein. For example, exon-skipping antisense oligonucleotides (ASOs) that correct missplicing can be used, e.g., as described in Siva et al., Nucleic Acid Ther. 2014 Feb. 1; 24(1): 69-86; Scotti and Swanson, Nature Reviews Genetics 17:19-32 (2016). For example, bicyclic-locked nucleic acids (LNAs), ethylene-bridged nucleic acids (ENAs), 2'-O-methyl phosphorothioate AO (2OME-PSs), peptide nucleic acids (PNAs), or phosphorodiamidate morpholino oligomers (PMOs) have been described that correct missplicing in clinical trials and animal models; see, e.g., Brolin and Shiraishi, Artif DNA PNA XNA. 2011 January-March; 2(1): 6-15; Scotti and Swanson, Nature Reviews Genetics 17:19-32 (2016); Touznik et al., Expert Opin Biol Ther. 2014 June; 14(6):809-19. The ASOs can be delivered, e.g., parenterally in liposomal complexes, e.g., cationic lipoplexes, or using a viral vector, e.g., a lentivirus, adenovirus, or adeno-associated virus. See e.g., Jarver et al., Nucleic Acid Ther. 2014; 24(1):37-47; Aartsma-Rus et al., Hum Gene Ther. 2014; 25(10):885-892, McNally and Wyatt, J Clin Invest. 2016 Apr. 1; 126(4):1236-8; Imbert et al., Genes 2017, 8(2), 51; doi:10.3390/genes8020051. Specific ASOs for use in exon 51 skipping therapy, e.g., in DMD, include PRO051 (2OME-PS, Netherlands) and AVI-4658 (PMO, UK). A plurality of ASOs can also be used, e.g., to induce exon skipping in multiple exons; see, e.g., Wood et al., Brain. 2010 April; 133(Pt 4):957-72 See also Fletcher et al., Mol Ther Nucleic Acids. 2012 October; 1(10): e48; McClorey et al., Curr Opin Pharmacol. 2005 Oct.; 5(5):529-34. Small molecule therapeutics can also be used, e.g., PTC124, a 284.24-Da, achiral, 1,2,4-oxadiazole linked to fluorobenzene and benzoic acid rings, which selectively induces ribosomal read-through of premature but not normal termination codons, see Welch et al., Nature 447: 87-91, 2007, and has been used in clinical trials for DMD.

EXAMPLES

The invention is further described in the following examples, which do not limit the scope of the invention described in the claims.

Example 1

The miR-128-1 microRNA is a Potential Disease Modifier and Therapeutic Target in DMD While essentially all disease treatments to date have focused on targeting functions or activity of genes and proteins, regulatory non-coding RNAs such as microRNAs (miRNAs) have recently come to the fore as potential modifiers and therapeutic targets in a range of diseases, including DMD. It was hypothesized that the miR-128-1 miRNA might represent an intriguing therapeutic target in DMD due to its regulation of skeletal muscle metabolism and direct targeting of several key modifiers downstream of dystrophin loss.

Relevant to this proposal and as alluded to above, we identified miR-128-1 as implicated in regulating a number of the genes shown to act as modifiers of DMD phenotypes, including PGC-1α, AMPKα2, SIRT1, JAG1 and Wnt7A, as well as other metabolic regulators such as PPARα, PPARγ, ULK1, CPT1β, and others. During studies of the effects of LNA ASOs targeting miR-128-1 in diet-induced obese mice (once-weekly tail-vein injection of 10 mg/kg of a 9mer all LNA ASO (SEQ ID NO:9) directed against the seed sequence of miR-128, for 16 weeks into high-fat (60% fat) diet-fed male C57BL/6J mice starting at 6 weeks of age), we observed marked beneficial energy metabolism-related effects in skeletal muscle, including increased mitochondrial numbers and elevated expression of energy expenditure genes such as PGC-1α, AMPKα2, CPT1β, and PPARα, several of which have been implicated as downstream modifiers of DMD pathologies as discussed above (FIGS. 1A-C).

Consistent with our findings of miR-128-1 as a central regulator of metabolic homeostasis in skeletal muscle, and with verified and predicted targets implicated as key modifiers of the etiology of DMD, members of our team (Kunkel et al.) have independently identified miR-128-1 as an important regulator of proliferation and differentiation in muscle side population (SP) cells[63], a cell type considered to represent muscle stem cells with high mesenchymal potential, and a possible muscular dystrophy therapy. They found in this study that expression of miR-128-1 is elevated in SP cells, but decreases during continued culture in vitro. Furthermore, over-expression of miR-128-1 inhibited SP cell proliferation and differentiation potential. These findings suggest that miR-128-1 contributes to the maintenance of the quiescent state of SP cells, and may act to prevent their regenerative differentiation potential.

Figure 8C:
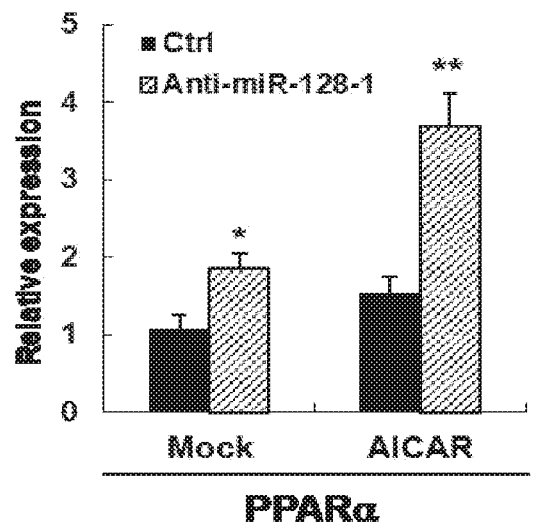
Figure 8D:
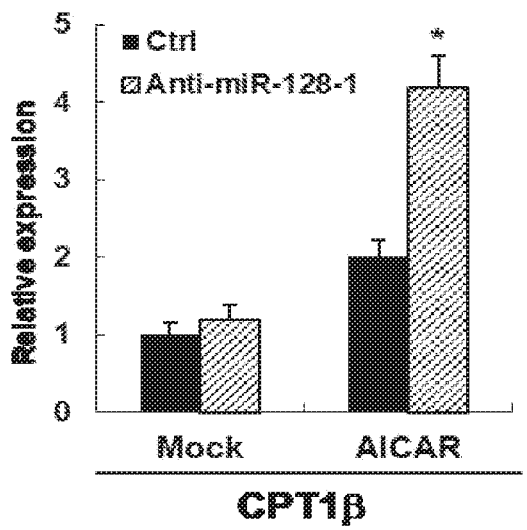
Figure 8E:
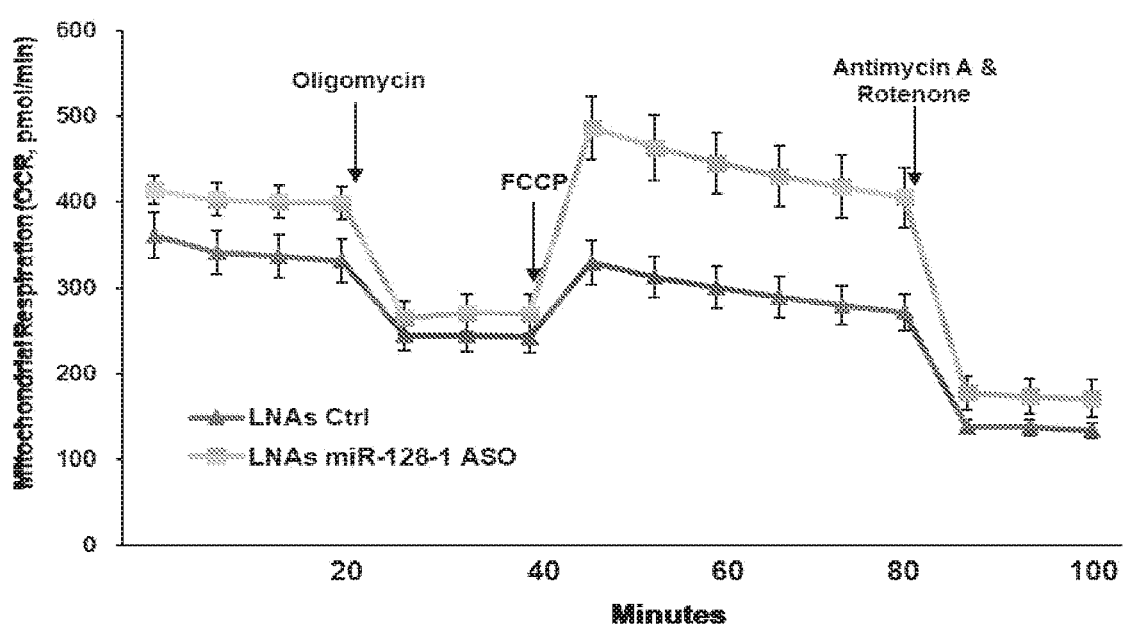
Figure 8F:
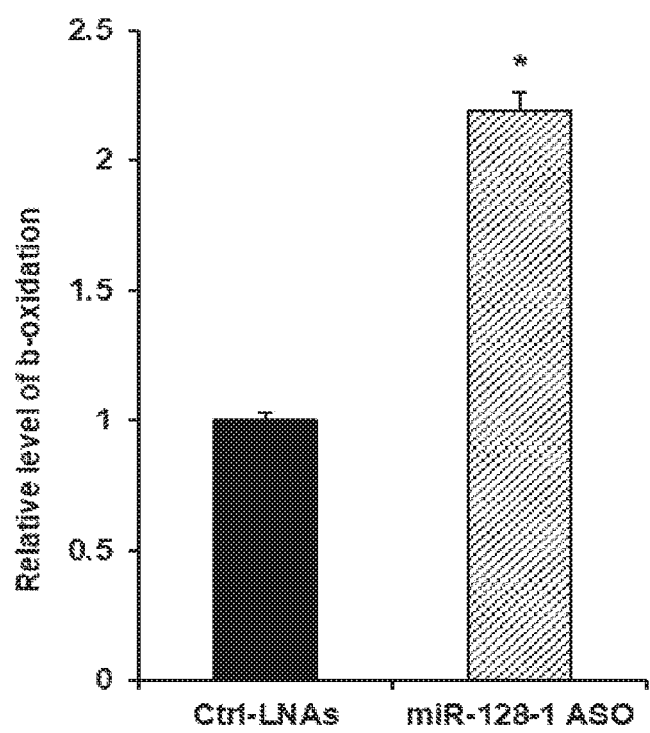

Over-expression and antisense targeting of miR-128-1 in differentiated mouse C2C12 myotubes results in altered expression of a number of predicted targets involved in controlling mitochondrial biogenesis and regulation of energy expenditure (FIGS. 8A-C).

Example 2

Evaluation of Downstream Effects of miR-128-1 Over-expression and Antisense Inhibition in Skeletal Muscle Cells As discussed above, abnormal mitochondrial function and defective autophagy/mitophagy has been implicated in DMD, and several rescue strategies such as PGC-1α over-expression, as well as AMPK and SIRT1 activation by metformin and resveratrol/nicotinamide riboside, respectively, act to promote mitochondrial health and numbers, as well as stimulating autophagy/mitophagy.

Figure 6B:
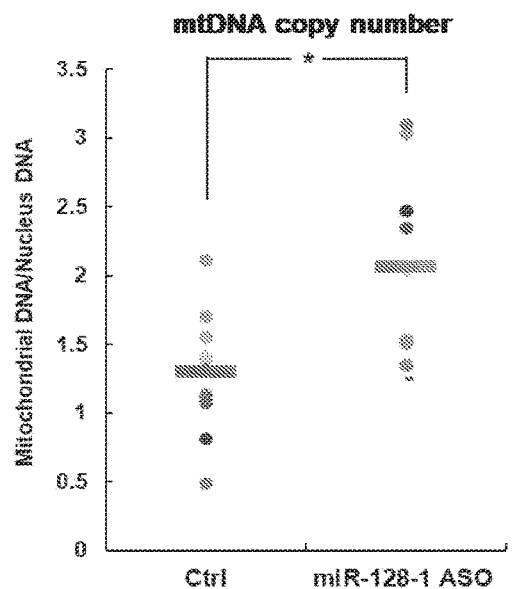
Figure 6C:
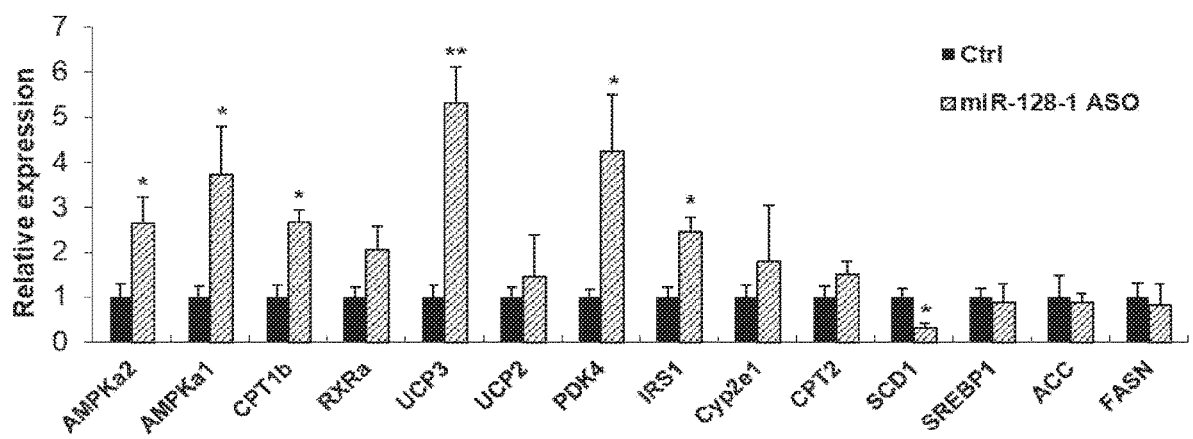
Figure 7A:
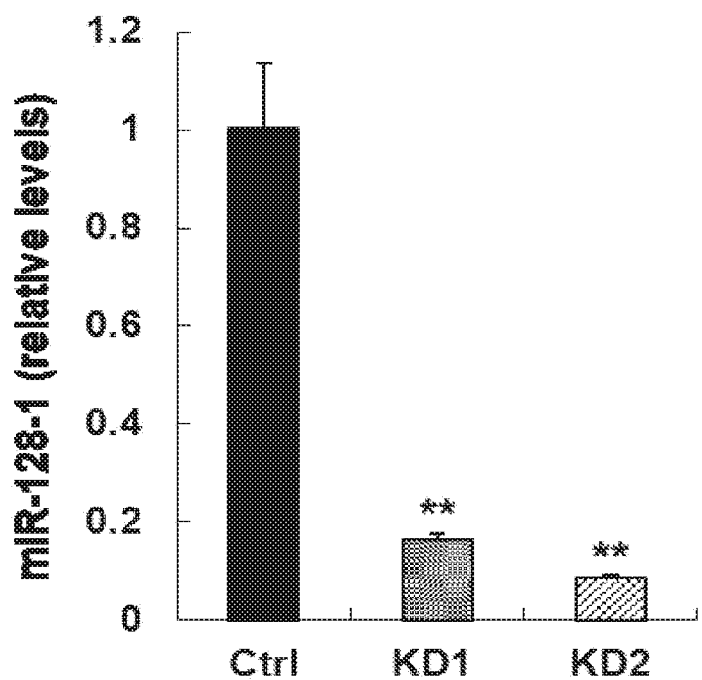
Figure 7B:
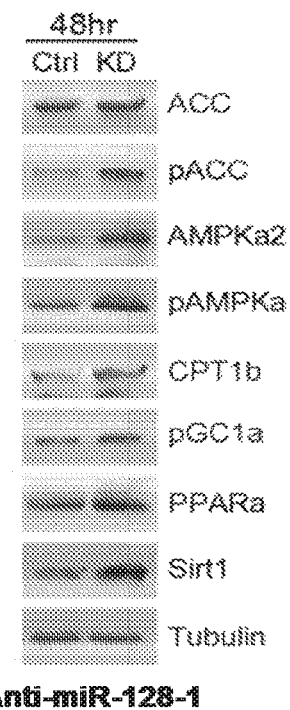

We have shown that antisense-mediated inhibition of miR-128-1 in diet-induced obese (DIO) mice results in an increase in skeletal muscle mitochondrial number, and elevated expression of several direct and indirect miR-128-1 regulated genes involved in mitochondrial biology and energy homeostasis (FIGS. 6A-C).

It was hypothesized that anti-miR-128-1 treatment might cooperate with agents that stimulate AMPK and SIRT1, such as AICAR/metformin and resveratrol/nicotinamide riboside, respectively. To determine the impact of anti-miR-128-1 treatment alone and in combination with these AMPK and sirtuin activators on metabolic health of muscle cell from normal individuals and DMD patients, we queried effects on muscle cell physiology, including AICAR-dependent increase in energy expenditure regulators, including AMPKα2, PGC-1α, PPARα, and CPT1β, as well as mitochondrial number (determined by levels of mitochondrial markers COXI-III) and morphology (visualized with MitoTracker Green), Seahorse studies of mitochondrial respiration as a read-out of mitochondrial health and bioenergetics output capacity, and autophagy (as judged by staining cells with the LC3 autophagy marker). We also determined the effects of miR-128-1 manipulations on additional metabolic parameters in muscle cells, such as fatty acid eta-oxidation as a read-out of mitochondrial activity. As a proof-of-principle study we have investigated the effect of anti-miR-128-1 treatment of C2C12 myoblasts, and indeed found potentiation of AICAR stimulation of energy regulators, elevated mitochondrial respiration, and increased fatty acid eta-oxidation upon miR-128-1 knock-down (FIGS. 8A-F), providing strong support for the success of the proposed studies.

Example 3 miR-128-1 Antisense Inhibition can Prevent Muscle Disease Progression in Dystrophin-deficient Zebrafish We performed a short-term study with the sapje-like zebrafish DMD model using candidate LNA ASOs. 100-200 embryos from mating pairs of heterozygous sapje-like mutant fish were injected with microneedle at the one cell stage on 0 dpf at 50 fmol dosage of anti-miR128-1 9mer or control LNA ASOs. The experiment was independently repeated three times. All plates containing embryos were incubated at 28° C. At 4dpf, the birefringence of all fish were assessed using a dissecting microscope and examined for black spots in the dorsal muscles (indicator of muscle myofiber weakness and myofiber disorganization) as shown in FIG. 9A. Since the muscle phenotype in these mutant fish is transmitted in a recessive manner, ~25% of the control offspring will exhibit the muscle birefringence phenotype. Our initial study showed that the 9mer-LNA ASO at 50 fmol consistently reduced the percentage of affected birefringence fish in sapje-like fish to 14% (FIG. 9B), and gene sequencing from the last experiment confirmed that >30% of dystrophin −/− fish exhibited normal muscle structure (FIG. 9C). In the initial screening DanioVision tracking system was used to monitor single zebrafish larvae movement in 24-well plates. At 5dpf Sapje-like fish after injection were monitored individually in a 24-well plate at 28° C. in the system for 20 mins after acclimation. Fish movement was tracked and mapped, and analyzed for swimming velocity and distance traveled.

Figure 10A:
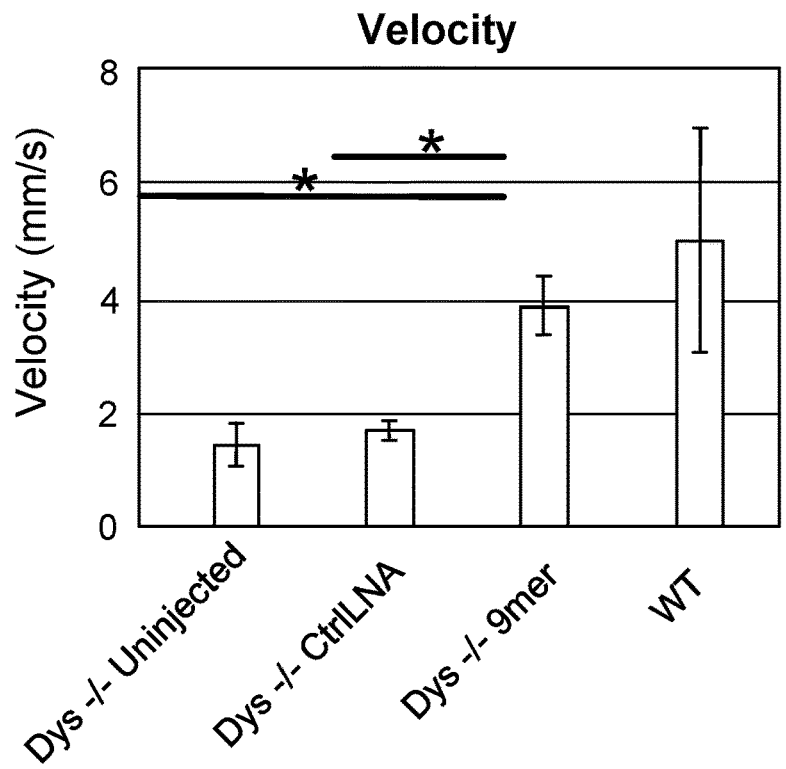
FIGS. 10A-B. Anti-miR128 9mer LNA significantly improved dystrophin−/− sapje-like fish activity. 9mer LNA significantly increased the velocity (10A) and the total distance (10B) of dystrophin−/− fish at 5dpf to a level comparable to wildtype fish.
Figure 10B:
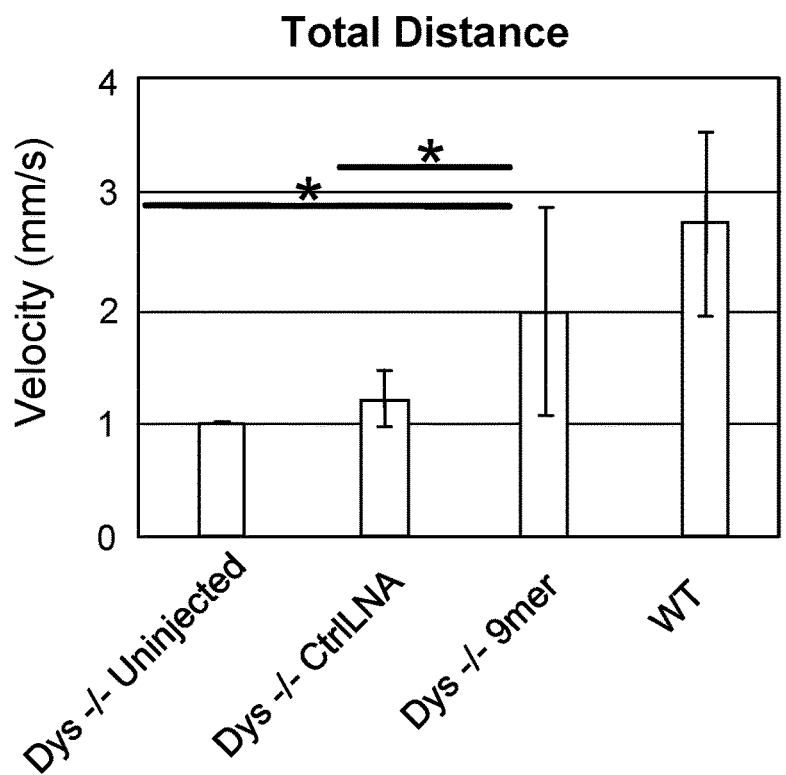

The results showed that the 9mer-LNA ASO significantly increased dystrophin−/− sapje-like fish activity to a level comparable to wild type zebrafish level (FIG. 10A-B). Taken together, these results demonstrate that there is efficacy of miR-128 inhibition in dystrophin−/− zebrafish and that we can optimize the dosage and treatment conditions to be able to distinguish between effective and non-effective treatments on the muscle phenotype in the zebrafish model of DMD.

Example 4

Anti-miR-128-1 LNA ASO Treatment of Mdx Mice

Figure 11A:
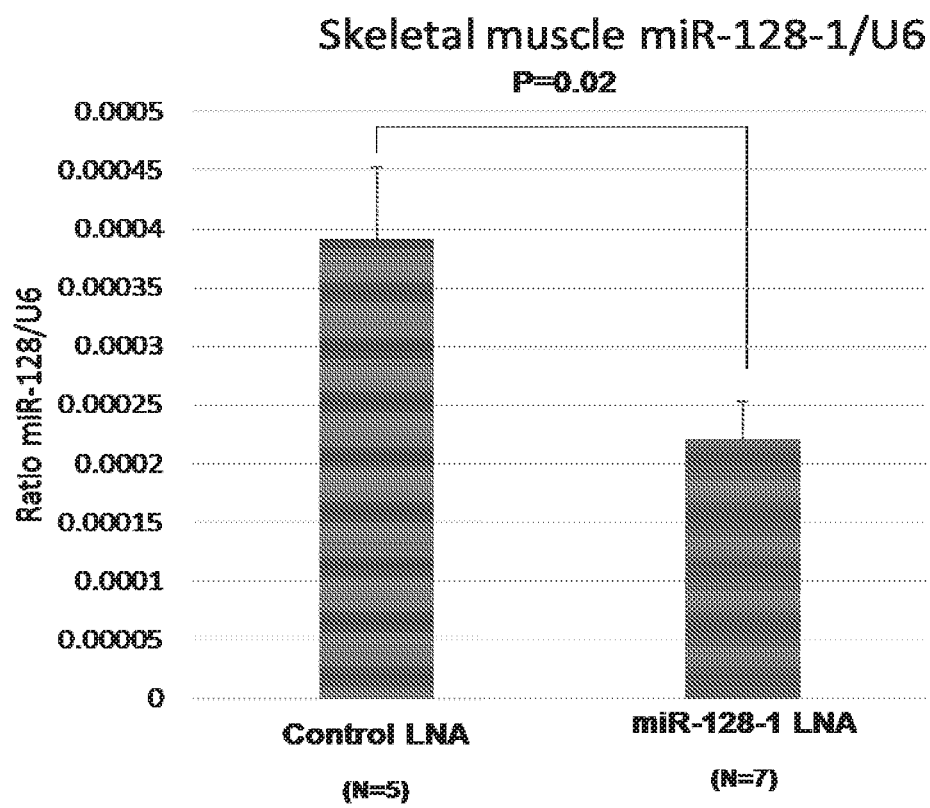
FIGS. 11A-C. Pilot study of LNA ASO treatment targeting miR-128-1 in the mdx mouse DMD model. 11A. Decreased miR-128-1 levels in TA muscle in response to anti-miR-128-1 LNA ASO treatment. 11B. Lowered circulating creatine kinase in anti-miR-128-1-treated mdx mice. 11C. Treatment with anti-miR-128-1 LNA ASOs resulted in increased grip strength in the two-limb hanging grip test.
Figure 11B:
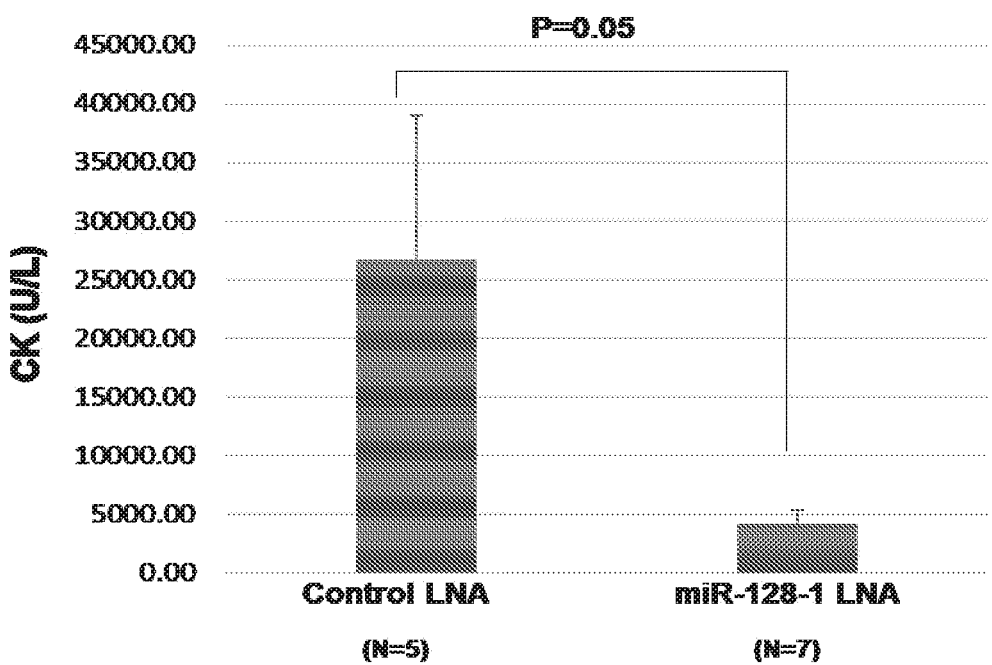
Figure 11C:
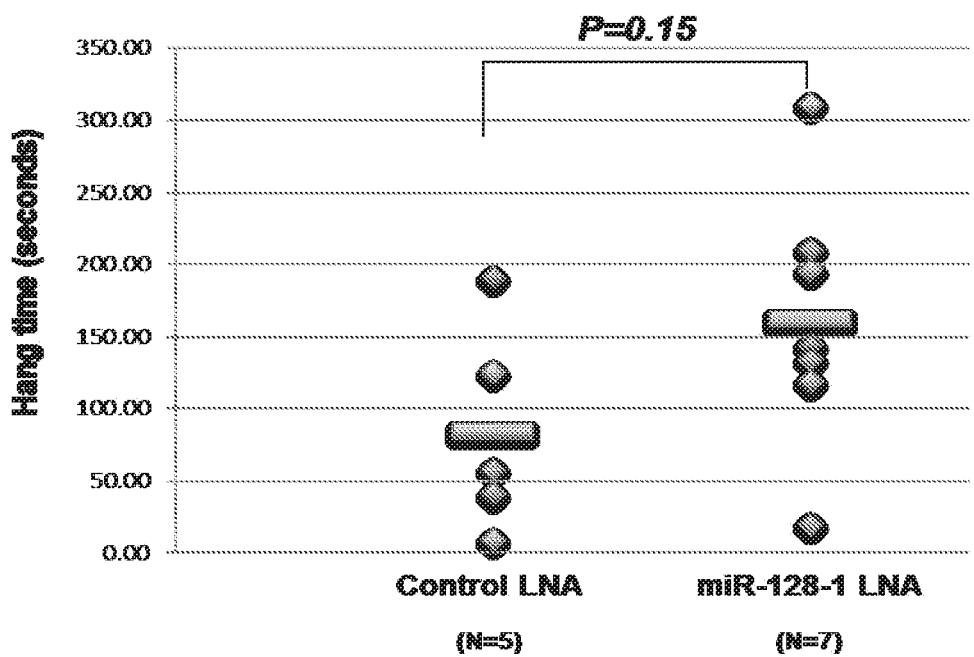

Additional experiments included treatment with potent and highly specific LNA ASOs targeting miR-128-1 and control scrambled LNA ASO in mdx male mice. Age-matched mice were injected subcutaneously with 10 mg/kg of LNA ASO (SEQ ID NO:8) in saline or scrambled control LNA ASO once-weekly starting at six weeks of age. Treatment continued for 10 weeks, with motor function assessment every two weeks during treatment, including by grip test and molecular analyses. As shown in FIG. 11A, anti-miR-128-1 treatment resulted in significant target engagement in skeletal muscle (TA), decreasing miR-128-1 levels significantly by ~50%. Consistent with miR-128-1 contributing to deleterious phenotypes in this DMD model, we observed a marked decrease in circulating creatine kinase (correlating with muscle damage and a hallmark of DMD) (FIG. 11B), as well as improvement in grip strength (FIG. 11C). These encouraging results support the use of anti-miR-128 LNA ASOs in DMD.

REFERENCES

1 Guiraud, S. et al. The Pathogenesis and Therapy of Muscular Dystrophies. Annu Rev Genomics Hum Genet 16, 281-308, doi:10.1146/annurev-genom-090314-025003 (2015).

2 Syed, Y. Y. Eteplirsen: First Global Approval. Drugs 76, 1699-1704, doi:10.1007/s40265-016-0657-1 (2016).

3 Schuh, R. A., Jackson, K C, Khairallah, R. J., Ward, C. W. & Spangenburg, E. E. Measuring mitochondrial respiration in intact single muscle fibers. Am J Physiol Regul Integr Comp Physiol 302, R712-719, doi:10.1152/ajpregu.00229.2011 (2012).

4 van Westering, T. L., Betts, C. A. & Wood, M. J. Current understanding of molecular pathology and treatment of cardiomyopathy in duchenne muscular dystrophy. Molecules 20, 8823-8855, doi:10.3390/molecules20058823 (2015).

5 Rybalka, E., Timpani, C. A., Cooke, M. B., Williams, A. D. & Hayes, A. Defects in mitochondrial ATP synthesis in dystrophin-deficient mdx skeletal muscles may be caused by complex I insufficiency. PLoS One 9, e115763, doi:10.1371/journal.pone.0115763 (2014).

6 Baron, D. et al. Immune response and mitochondrial metabolism are commonly deregulated in DMD and aging skeletal muscle. PLoS One 6, e26952, doi:10.1371/journal.pone.0026952 (2011).

7 Percival, J. M., Siegel, M. P., Knowels, G. & Marcinek, D. J. Defects in mitochondrial localization and ATP synthesis in the mdx mouse model of Duchenne muscular dystrophy are not alleviated by PDE5 inhibition. Hum Mol Genet 22, 153-167, doi:10.1093/hmg/dds415 (2013).

8 Kyrychenko, V., Polakova, E., Janicek, R. & Shirokova, N. Mitochondrial dysfunctions during progression of dystrophic cardiomyopathy. Cell Calcium 58, 186-195, doi: 10.1016/j.ceca.2015.04.006 (2015).

9 Timpani, C. A., Hayes, A. & Rybalka, E. Revisiting the dystrophin-ATP connection: How half a century of research still implicates mitochondrial dysfunction in Duchenne Muscular Dystrophy aetiology. Med Hypotheses 85, 1021-1033, doi:10.1016/j.mehy.2015.08.015 (2015).

10 De Palma, C., Perrotta, C., Pellegrino, P., Clementi, E. & Cervia, D. Skeletal muscle homeostasis in duchenne muscular dystrophy: modulating autophagy as a promising therapeutic strategy. Front Aging Neurosci 6, 188, doi: 10.3389/fnagi.2014.00188 (2014).

11 Pal, R. et al. Src-dependent impairment of autophagy by oxidative stress in a mouse model of Duchenne muscular dystrophy. Nat Commun 5, 4425, doi:10.1038/ncomms5425 (2014).

12 Sandri, M., Coletto, L., Grumati, P. & Bonaldo, P. Misregulation of autophagy and protein degradation systems in myopathies and muscular dystrophies. J Cell Sci 126, 5325-5333, doi:10.1242/jcs.114041 (2013).

13 Bonaldo, P. & Sandri, M. Cellular and molecular mechanisms of muscle atrophy. Dis Model Mech 6, 25-39, doi:10.1242/dmm.010389 (2013).

14 Whitehead, N P Enhanced autophagy as a potential mechanism for the improved physiological function by simvastatin in muscular dystrophy. Autophagy 12, 705-706, doi:10.1080/15548627.2016.1144005 (2016).

15 Fiacco, E. et al. Autophagy regulates satellite cell ability to regenerate normal and dystrophic muscles. Cell Death Differ 23, 1839-1849, doi:10.1038/cdd.2016.70 (2016).

16 Moulin, M. & Ferreiro, A. Muscle redox disturbances and oxidative stress as pathomechanisms and therapeutic targets in early-onset myopathies. Semin Cell Dev Biol 64, 213-223, doi:10.1016/j.semcdb.2016.08.003 (2017).

17 Terrill, J. R. et al. Oxidative stress and pathology in muscular dystrophies: focus on protein thiol oxidation and dysferlinopathies. FEBS J 280, 4149-4164, doi:10.1111/febs.12142 (2013).

18 Whitehead, N. P., Yeung, E. W. & Allen, D. G. Muscle damage in mdx (dystrophic) mice: role of calcium and reactive oxygen species. Clin Exp Pharmacol Physiol 33, 657-662, doi:10.1111/j.1440-1681.2006.04394.x (2006).

19 Kim, H. K. et al. Analysis of fatty infiltration and inflammation of the pelvic and thigh muscles in boys with Duchenne muscular dystrophy (DMD): grading of disease involvement on MR imaging and correlation with clinical assessments. Pediatr Radiol 43, 1327-1335, doi:10.1007/s00247-013-2696-z (2013).

20 Serrano, A. L. & Munoz-Canoves, P. Fibrosis development in early-onset muscular dystrophies: Mechanisms and translational implications. Semin Cell Dev Biol 64, 181-190, doi:10.1016/j.semcdb.2016.09.013 (2017).

21 Rosenberg, A. S. et al. Immune-mediated pathology in Duchenne muscular dystrophy. Science translational medicine 7, 299rv294, doi:10.1126/scitranslmed.aaa7322 (2015).

22 Kotelnikova, E., Shkrob, M. A., Pyatnitskiy, M. A., Ferlini, A. & Daraselia, N. Novel approach to meta-analysis of microarray datasets reveals muscle remodeling-related drug targets and biomarkers in Duchenne muscular dystrophy. PLoS Comput Biol 8, e1002365, doi:10.1371/journal.pcbi.1002365 (2012).

23 Liu, J. et al. Coupling of mitochondrial function and skeletal muscle fiber type by a miR-499/Fnipl/AMPK circuit. EMBO molecular medicine 8, 1212-1228, doi:10.15252/emmm.201606372 (2016).

24 Camerino, G. M. et al. Gene expression in mdx mouse muscle in relation to age and exercise: aberrant mechanical-metabolic coupling and implications for pre-clinical studies in Duchenne muscular dystrophy. Hum Mol Genet 23, 5720-5732, doi:10.1093/hmg/ddu287 (2014).

25 Chan, M. C. et al. Post-natal induction of PGC-1alpha protects against severe muscle dystrophy independently of utrophin. Skelet Muscle 4, 2, doi:10.1186/2044-5040-4-2 (2014).

26 Hollinger, K. et al. Rescue of dystrophic skeletal muscle by PGC-1alpha involves restored expression of dystrophin-associated protein complex components and satellite cell signaling. Am J Physiol Regul Integr Comp Physiol 305, R13-23, doi:10.1152/ajpregu.00221.2012 (2013).

27 Selsby, J. T., Morine, K. J., Pendrak, K., Barton, E. R. & Sweeney, H. L. Rescue of dystrophic skeletal muscle by PGC-1alpha involves a fast to slow fiber type shift in the mdx mouse. PLoS One 7, e30063, doi:10.1371/journal.pone.0030063 (2012).

28 Handschin, C. et al. Skeletal muscle fiber-type switching, exercise intolerance, and myopathy in PGC-1alpha muscle-specific knock-out animals. J Biol Chem 282, 30014-30021, doi:10.1074/jbc.M704817200 (2007).

29 Handschin, C. et al. PGC-1alpha regulates the neuromuscular junction program and ameliorates Duchenne muscular dystrophy. Genes Dev 21, 770-783, doi:10.1101/gad.1525107 (2007).

30 Guevel, L. et al. Quantitative proteomic analysis of dystrophic dog muscle. J Proteome Res 10, 2465-2478, doi:10.1021/pr2001385 (2011).

31 De Arcangelis, V. et al. Pathways Implicated in Tadalafil Amelioration of Duchenne Muscular Dystrophy. J Cell Physiol 231, 224-232, doi:10.1002/jcp.25075 (2016).

32 Godin, R. et al. Peroxisome proliferator-activated receptor gamma coactivator1-gene alpha transfer restores mitochondrial biomass and improves mitochondrial calcium handling in post-necrotic mdx mouse skeletal muscle. J Physiol 590, 5487-5502, doi:10.1113/jphysiol.2012.240390 (2012).

33 Garbincius, J. F. & Michele, D. E. Dystrophin-glycoprotein complex regulates muscle nitric oxide production through mechanoregulation of AMPK signaling. Proc Natl Acad Sci USA 112, 13663-13668, doi:10.1073/pnas.1512991112 (2015).

34 Ljubicic, V. et al. Chronic AMPK activation evokes the slow, oxidative myogenic program and triggers beneficial adaptations in mdx mouse skeletal muscle. Hum Mol Genet 20, 3478-3493, doi:10.1093/hmg/ddr265 (2011).

35 Al-Rewashdy, H., Ljubicic, V., Lin, W., Renaud, J. M. & Jasmin, B. J. Utrophin A is essential in mediating the functional adaptations of mdx mouse muscle following chronic AMPK activation. Hum Mol Genet 24, 1243-1255, doi:10.1093/hmg/ddu535 (2015).

36 Ljubicic, V. & Jasmin, B. J. AMP-activated protein kinase at the *nexus* of therapeutic skeletal muscle plasticity in Duchenne muscular dystrophy. Trends Mol Med 19, 614-624, doi:10.1016/j.molmed.2013.07.002 (2013).

37 Pauly, M. et al. AMPK activation stimulates autophagy and ameliorates muscular dystrophy in the mdx mouse diaphragm. Am J Pathol 181, 583-592, doi:10.1016/j.ajpath.2012.04.004 (2012).

38 Chalkiadaki, A., Igarashi, M., Nasamu, A. S., Knezevic, J. & Guarente, L. Muscle-specific SIRT1 gain-of-function increases slow-twitch fibers and ameliorates pathophysiology in a mouse model of duchenne muscular dystrophy. PLoS genetics 10, e1004490, doi:10.1371/journal.pgen.1004490 (2014).

39 Kuno, A. & Horio, Y. SIRT1: A Novel Target for the Treatment of Muscular Dystrophies. Oxid Med Cell Longev 2016, 6714686, doi:10.1155/2016/6714686 (2016).

40 Choi, M. H., Ow, J. R., Yang, N. D. & Taneja, R. Oxidative Stress-Mediated Skeletal Muscle Degeneration: Molecules, Mechanisms, and Therapies. Oxid Med Cell Longev 2016, 6842568, doi:10.1155/2016/6842568 (2016).

41 Miura, P. et al. Pharmacological activation of PPAR-beta/delta stimulates utrophin A expression in skeletal muscle fibers and restores sarcolemmal integrity in mature mdx mice. Hum Mol Genet 18, 4640-4649, doi:10.1093/hmg/ddp431 (2009).

42 Gordon, B. S., Delgado Diaz, D. C. & Kostek, M. C. Resveratrol decreases inflammation and increases utrophin gene expression in the mdx mouse model of Duchenne muscular dystrophy. Clin Nutr 32, 104-111, doi:10.1016/j.clnu.2012.06.003 (2013).

43 Peladeau, C. et al. Combinatorial therapeutic activation with heparin and AICAR stimulates additive effects on utrophin A expression in dystrophic muscles. Hum Mol Genet 25, 24-43, doi:10.1093/hmg/ddv444 (2016).

44 Hafner, P. et al. Improved Muscle Function in Duchenne Muscular Dystrophy through L-Arginine and Metformin: An Investigator-Initiated, Open-Label, Single-Center, Proof-Of-Concept-Study. PLoS One 11, e0147634, doi:10.1371/journal.pone.0147634 (2016).

45 Bastin, J. & Djouadi, F. Resveratrol and Myopathy. Nutrients 8, doi:10.3390/nu8050254 (2016).

46 Hori, Y. S. et al. Resveratrol ameliorates muscular pathology in the dystrophic mdx mouse, a model for Duchenne muscular dystrophy. J Pharmacol Exp Ther 338, 784-794, doi:10.1124/jpet.111.183210 (2011).

47 Kuno, A. et al. Resveratrol improves cardiomyopathy in dystrophin-deficient mice through SIRT1 protein-mediated modulation of p300 protein. J Biol Chem 288, 5963-5972, doi:10.1074/jbc.M112.392050 (2013).

48 Kuno, A., Tanno, M. & Horio, Y. The effects of resveratrol and SIRT1 activation on dystrophic cardiomyopathy. Ann N Y Acad Sci 1348, 46-54, doi:10.1111/nyas.12812 (2015).

49 Capogrosso, R. F. et al. Assessment of resveratrol, apocynin and taurine on mechanical-metabolic uncoupling and oxidative stress in a mouse model of duchenne muscular dystrophy: A comparison with the gold standard, alpha-methyl prednisolone. Pharmacol Res 106, 101-113, doi:10.1016/j.phrs.2016.02.016 (2016).

50 Ryu, D. et al. NAD+ repletion improves muscle function in muscular dystrophy and counters global PARylation. Science translational medicine 8, 361ra139, doi:10.1126/scitranslmed.aaf5504 (2016).

51 Vieira, N. M. et al. Jagged 1 Rescues the Duchenne Muscular Dystrophy Phenotype. Cell 163, 1204-1213, doi:10.1016/j.cell.2015.10.049 (2015).

52 von Maltzahn, J., Renaud, J. M., Parise, G. & Rudnicki, M. A. Wnt7a treatment ameliorates muscular dystrophy. Proc Natl Acad Sci USA 109, 20614-20619, doi:10.1073/pnas.1215765109 (2012).

53 Ambros, V. The functions of animal microRNAs. Nature 431, 350-355, doi:10.1038/nature02871 (2004).

54 Bartel, D. P. MicroRNAs: genomics, biogenesis, mechanism, and function. Cell 116, 281-297 (2004).

55 Bartel, D. P. MicroRNAs: target recognition and regulatory functions. Cell 136, 215-233, doi:10.1016/j.cell.2009.01.002 (2009).

56 Hertel, J. et al. The expansion of the metazoan microRNA repertoire. BMC genomics 7, 25, doi:10.1186/1471-2164-7-25 (2006).

57 Lewis, B. P., Burge, C. B. & Bartel, D. P. Conserved seed pairing, often flanked by adenosines, indicates that thousands of human genes are microRNA targets. Cell 120, 15-20, doi:10.1016/j.cell.2004.12.035 (2005).

58 Goedeke, L. et al. MicroRNA-148a regulates LDL receptor and ABCA1 expression to control circulating lipoprotein levels. Nat Med 21, 1280-1289, doi:10.1038/nm.3949 (2015).

59 Najafi-Shoushtari, S. H. et al. MicroRNA-33 and the SREBP host genes cooperate to control cholesterol homeostasis. Science 328, 1566-1569, doi:10.1126/science.1189123 (2010).

60 Rottiers, V. & Naar, A. M. MicroRNAs in metabolism and metabolic disorders. Nat Rev Mol Cell Biol 13, 239-250, doi:10.1038/nrm3313 (2012).

61 Rottiers, V. et al. Pharmacological inhibition of a microRNA family in nonhuman primates by a seed-targeting 8-mer antimiR. Science translational medicine 5, 212ra162, doi:10.1126/scitranslmed.3006840 (2013).

62 Wagschal, A. et al. Genome-wide identification of microRNAs regulating cholesterol and triglyceride homeostasis. Nat Med 21, 1290-1297, doi:10.1038/nm.3980 (2015).

63 Motohashi, N., Alexander, M. S., Casar, J. C. & Kunkel, L. M. Identification of a novel microRNA that regulates the proliferation and differentiation in muscle side population cells. Stem Cells Dev 21, 3031-3043, doi:10.1089/scd.2011.0721 (2012).

64 Motohashi, N. et al. Regulation of IRS1/Akt insulin signaling by microRNA-128a during myogenesis. J Cell Sci 126, 2678-2691, doi:10.1242/jcs.119966 (2013).

65 Alexander, M. S. et al. MicroRNA-199a is induced in dystrophic muscle and affects WNT signaling, cell proliferation, and myogenic differentiation. Cell Death Differ 20, 1194-1208, doi:10.1038/cdd.2013.62 (2013).

66 Maciotta, S. et al. Hmgb3 is regulated by microRNA-206 during muscle regeneration. PLoS One 7, e43464, doi:10.1371/journal.pone.0043464 (2012).

67 van Rooij, E. & Kauppinen, S. Development of microRNA therapeutics is coming of age. EMBO molecular medicine 6, 851-864, doi:10.15252/emmm.201100899 (2014).

68 Kauppinen, S., Vester, B. & Wengel, J. Locked nucleic acid: high-affinity targeting of complementary RNA for RNomics. Handb Exp Pharmacol, 405-422 (2006).

69 Lindow, M. & Kauppinen, S. Discovering the first microRNA-targeted drug. J Cell Biol 199, 407-412, doi:10.1083/jcb.201208082 (2012).

70 Vallejo-Illarramendi, A., Toral-Ojeda, I., Aldanondo, G. & Lopez de Munain, A. Dysregulation of calcium homeostasis in muscular dystrophies. Expert Rev Mol Med 16, e16, doi:10.1017/erm.2014.17 (2014).

71 Alexander, M. S. et al. Regulation of DMD pathology by an ankyrin-encoded miRNA. Skelet Muscle 1, 27, doi:10.1186/2044-5040-1-27 (2011).

72 Guyon, J. R. et al. Modeling human muscle disease in zebrafish. Biochim Biophys Acta 1772, 205-215, doi:10.1016/j.bbadis.2006.07.003 (2007).

73 Widrick, J. J. et al. Muscle dysfunction in a zebrafish model of Duchenne muscular dystrophy. Physiol Genomics, physiolgenomics 00088 02016, doi:10.1152/physiolgenomics.00088.2016 (2016).

74 Kawahara, G. et al. Dystrophic muscle improvement in zebrafish via increased heme oxygenase signaling. Hum Mol Genet 23, 1869-1878, doi:10.1093/hmg/ddt579 (2014).

75 Kawahara, G. et al. Drug screening in a zebrafish model of Duchenne muscular dystrophy. Proc Natl Acad Sci USA 108, 5331-5336, doi:10.1073/pnas.1102116108 (2011).

76 Stedman, H. H. et al. The mdx mouse diaphragm reproduces the degenerative changes of Duchenne muscular dystrophy. Nature 352, 536-539, doi:10.1038/352536a0 (1991).

77 Beastrom, N. et al. mdx((5)cv) mice manifest more severe muscle dysfunction and diaphragm force deficits than do mdx Mice. Am J Pathol 179, 2464-2474, doi:10.1016/j.ajpath.2011.07.009 (2011).

78 Chamberlain, J. S., Metzger, J., Reyes, M., Townsend, D. & Faulkner, J. A. Dystrophin-deficient mdx mice display a reduced life span and are susceptible to spontaneous rhabdomyosarcoma. FASEB journal: official publication of the Federation of American Societies for Experimental Biology 21, 2195-2204, doi:10.1096/fj.06-7353com (2007).

79 Bulfield, G., Siller, W. G., Wight, P. A. & Moore, K. J. X chromosome-linked muscular dystrophy (mdx) in the mouse. Proc Natl Acad Sci USA 81, 1189-1192 (1984).

80 Carnwath, J. W. & Shotton, D. M. Muscular dystrophy in the mdx mouse: histopathology of the soleus and extensor digitorum longus muscles. J Neurol Sci 80, 39-54 (1987).

81 Tanabe, Y., Esaki, K. & Nomura, T. Skeletal muscle pathology in X chromosome-linked muscular dystrophy (mdx) mouse. Acta Neuropathol 69, 91-95 (1986).

82 Torres, L. F. & Duchen, L. W. The mutant mdx: inherited myopathy in the mouse. Morphological studies of nerves, muscles and end-plates. Brain 110 (Pt 2), 269-299 (1987).

83 Dangain, J. & Vrbova, G. Muscle development in mdx mutant mice. Muscle Nerve 7, 700-704, doi:10.1002/mus.880070903 (1984).

84 Muntoni, F., Mateddu, A., Marchei, F., Clerk, A. & Serra, G. Muscular weakness in the mdx mouse. J Neurol Sci 120, 71-77 (1993).

85 Grounds, M. D., Radley, H. G., Lynch, G. S., Nagaraju, K. & De Luca, A. Towards developing standard operating procedures for pre-clinical testing in the mdx mouse model of Duchenne muscular dystrophy. Neurobiol Dis 31, 1-19, doi:10.1016/j.nbd.2008.03.008 (2008).

86 Spurney, C. F. et al. Preclinical drug trials in the mdx mouse: assessment of reliable and sensitive outcome measures. Muscle Nerve 39, 591-602, doi:10.1002/mus.21211 (2009).

87 Chapman, V. M., Miller, D. R., Armstrong, D. & Caskey, C. T. Recovery of induced mutations for X chromosome-linked muscular dystrophy in mice. Proc Natl Acad Sci USA 86, 1292-1296 (1989).

88 Araki, E. et al. Targeted disruption of exon 52 in the mouse dystrophin gene induced muscle degeneration similar to that observed in Duchenne muscular dystrophy. Biochem Biophys Res Commun 238, 492-497, doi:10.1006/bbrc.1997.7328 (1997).

89 Fukada, S. et al. Genetic background affects properties of satellite cells and mdx phenotypes. Am J Pathol 176, 2414-2424, doi:10.2353/ajpath.2010.090887 (2010).

90 Im, W. B. et al. Differential expression of dystrophin isoforms in strains of mdx mice with different mutations. Hum Mol Genet 5, 1149-1153 (1996).

91 Danko, I., Chapman, V. & Wolff, J. A. The frequency of revertants in mdx mouse genetic models for Duchenne muscular dystrophy. Pediatr Res 32, 128-131, doi:10.1203/00006450-199207000-00025 (1992).

92 Geary, R. S., Norris, D., Yu, R. & Bennett, C. F. Pharmacokinetics, biodistribution and cell uptake of antisense oligonucleotides. Adv Drug Deliv Rev 87, 46-51, doi:10.1016/j.addr.2015.01.008 (2015).

93 Obad, S. et al. Silencing of microRNA families by seed-targeting tiny LNAs. Nat Genet 43, 371-378, doi:10.1038/ng.786 (2011).

94 Stenvang, J., Petri, A., Lindow, M., Obad, S. & Kauppinen, S. Inhibition of microRNA function by antimiR oligonucleotides. Silence 3, 1, doi:10.1186/1758-907X-3-1 (2012).

95 Tan, C. L. et al. MicroRNA-128 governs neuronal excitability and motor behavior in mice. Science 342, 1254-1258, doi:10.1126/science.1244193 (2013).

96 Kobayashi, Y. M. et al. Sarcolemma-localized nNOS is required to maintain activity after mild exercise. Nature 456, 511-515, doi:10.1038/nature07414 (2008).

97 Arany, Z. PGC-1 coactivators and skeletal muscle adaptations in health and disease. Curr Opin Genet Dev 18, 426-434, doi:10.1016/j.gde.2008.07.018 (2008).

98 Khan, T. et al. Silencing Myostatin Using Cholesterol-conjugated siRNAs Induces Muscle Growth. Mol Ther Nucleic Acids 5, e342, doi:10.1038/mtna.2016.55 (2016).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject who has Duchenne muscular dystrophy (DMD) or Becker muscular dystrophy (BMD), the method comprising administering to the subject a therapeutically effective amount of an inhibitory nucleic acid that is complementary to all or part of any of SEQ ID NOs: 1-6.

2. A method of increasing muscle mass, or reducing or delaying muscle loss, in a subject who has Duchenne muscular dystrophy (DMD) or Becker muscular dystrophy (BMD), the method comprising administering to the subject a therapeutically effective amount of an inhibitory nucleic acid that is complementary to all or part of any of SEQ ID NOs: 1-6.

3. A method of treating, or reducing risk of developing, dilated cardiomyopathy (DCM) in a subject, optionally wherein the subject has Duchenne muscular dystrophy (DMD) or Becker muscular dystrophy (BMD), the method comprising administering to the subject an inhibitory nucleic acid sequence that is complementary to all or part of any of SEQ ID NOs: 1-6.

4. The method of claim 1, wherein the inhibitory nucleic acid is complementary to all or part of SEQ ID NO:2.

5. The method of claim 1, wherein the inhibitory nucleic acid is complementary to at least nucleotides 2-7

(5'-CACAGU-3') of SEQ ID NO: 3.

6. The method of claim 1, wherein the inhibitory nucleic acid is an antisense oligonucleotide.

7. The method of claim 6, wherein the antisense oligonucleotide comprises a sequence that is complementary to SEQ ID NO:3.

8. The method of claim 6, wherein the antisense oligonucleotide is an antagomir.

9. The method of claim 1, wherein the inhibitory nucleic acid is an interfering RNA.

10. The method of claim 9, wherein the interfering RNA is a small hairpin RNA (shRNA) or small interfering RNA (siRNA).

11. The method of claim 1, wherein the inhibitory nucleic acid sequence inhibits post-transcriptional processing of SEQ ID NO: 1 or 5.

12. The method of claim 1, wherein the subject has DMD.

13. The method of claim 12, further comprising selecting a subject on the basis that they have DMD.

14. The method of claim 1, wherein the inhibitory nucleic acid has at least one locked nucleotide.

15. The method of claim 1, wherein the inhibitory nucleic acid has a phosphorothioate backbone.

16. The method of claim 1, wherein the inhibitory nucleic acid is or comprises (SEQ ID NO: 10)
TTCACTGTG or (SEQ ID NO: 11)
GGTTCACTGTG, 17. The method of claim 16, wherein at least half of the nucleic acids are locked.

18. The method of claim 16, wherein all of the nucleic acids are locked.

19. The method of claim 16, wherein the backbone is a phosphorothioate backbone.

20. The method of claim 1, wherein the inhibitory nucleic acid is or comprises (SEQ ID NO: 8)
+G*+G*+T*+T*C*A*C*+T*+G*+T*+G.

wherein+represents an LNA nucleotide and*represents a phosphorothioate linkage.

21. The method of claim 20, wherein the inhibitory nucleic acid is administered at a dose of 1-20 mg/kg.

22. The method of claim 21, wherein the inhibitory nucleic acid is administered once or twice per month.

23. An inhibitory nucleic acid, which is or comprises (SEQ ID NO: 8)
+G*+G*+T*+T*C*A*C*+T*+G*+T*+G wherein+represents an LNA nucleotide and*represents a phosphorothioate linkage.

24. A pharmaceutical composition comprising the inhibitory nucleic acid of claim 23.

* * * * *

UNITED STATES PATENT AND TRADEMARK OFFICE
CERTIFICATE OF CORRECTION

PATENT NO. : 10,626,395 B2
APPLICATION NO. : 16/345635
DATED : April 21, 2020
INVENTOR(S) : Anders M. Naar, Sakari Kauppinen and Andreas Petri It is certified that error appears in the above-identified patent and that said Letters Patent is hereby corrected as shown below:

In the Claims

In Column 36, Line 30 (approx.), in Claim 16, delete "GGTTCACTGTG," and insert -- GGTTCACTGTG. --

In Column 36, Line 43 (approx.), in Claim 20, delete "wherein+represents" and insert -- wherein + represents --

In Column 36, Line 43 (approx.), in Claim 20, delete "and*represents" and insert -- and * represents --

In Column 36, Line 53 (approx.), in Claim 23, delete "wherein+represents" and insert -- wherein + represents --

In Column 36, Line 53 (approx.), in Claim 23, delete "and*represents" and insert -- and * represents --

Signed and Sealed this
Twenty-fifth Day of August, 2020

Andrei Iancu
*Director of the United States Patent and Trademark Office*